(12) United States Patent
Kannan et al.

(10) Patent No.: US 10,847,265 B2
(45) Date of Patent: Nov. 24, 2020

(54) SYSTEMS AND METHODS FOR RESPONDING TO HEALTHCARE INQUIRIES

(71) Applicant: Curai, Inc., Palo Alto, CA (US)

(72) Inventors: Anitha Kannan, Saratoga, CA (US); Murali Ravuri, Sunnyvale, CA (US); Vitor Rodrigues, Los Gatos, CA (US); Vignesh Venkataraman, Cupertino, CA (US); Geoffrey Tso, San Carlos, CA (US); Neal Khosla, Portola Valley, CA (US); Neil Hunt, Los Altos, CA (US); Xavier Amatriain, Los Gatos, CA (US); Manish Chablani, San Carlos, CA (US); David Sontag, Brookline, MA (US); Viraj Uday Prabhu, Atlanta, GA (US)

(73) Assignee: Curai, Inc., Palo Alto, CA (US)

( * ) Notice: Subject to any disclaimer, the term of this patent is extended or adjusted under 35 U.S.C. 154(b) by 44 days.

(21) Appl. No.: 16/266,784

(22) Filed: Feb. 4, 2019

(65) Prior Publication Data
US 2019/0311814 A1    Oct. 10, 2019

Related U.S. Application Data

(63) Continuation-in-part of application No. 16/265,799, filed on Feb. 1, 2019.
(Continued)

(51) Int. Cl.
*G16H 50/20* (2018.01)
*G16H 10/60* (2018.01)
(Continued)

(52) U.S. Cl.
CPC .............. *G16H 50/20* (2018.01); *G16H 10/20* (2018.01); *G16H 10/60* (2018.01); *G16H 50/30* (2018.01); *G16H 70/60* (2018.01); *G16H 80/00* (2018.01)

(58) Field of Classification Search
CPC ........ G06Q 50/22; G06Q 50/24; G06F 19/30; G06F 19/32; G06F 19/325; G06F 19/34;
(Continued)

(56) References Cited

U.S. PATENT DOCUMENTS

| | | |
|---|---|---|
| 7,149,756 B1 | 12/2006 | Schmitt et al. |
| 7,801,591 B1 | 9/2010 | Shusterman |

(Continued)

FOREIGN PATENT DOCUMENTS

| | | |
|---|---|---|
| WO | WO-2015/183699 A1 | 12/2015 |
| WO | WO-2016/126678 A1 | 8/2016 |

(Continued)

OTHER PUBLICATIONS

Prabhu et al., Prototypical Clustering Networks for Dermatological Disease Diagnosis, arXiv.org, Columbia University, 1811.03066v1, Nov. 7, 2018, 12 pages.*
(Continued)

*Primary Examiner* — Jason S Tiedeman
(74) *Attorney, Agent, or Firm* — Wilmer Cutler Pickering Hale and Dorr LLP

(57) ABSTRACT

Techniques for responding to a healthcare inquiry from a user are disclosed. In one particular embodiment, the techniques may be realized as a method for responding to a healthcare inquiry from a user, according to a set of instructions stored on a memory of a computing device and executed by a processor of the computing device, the method comprising the steps of: classifying an intent of the user based on the healthcare inquiry; identifying the intent as
(Continued)

a need to obtain a dermatological diagnosis or treatment; soliciting, from the user and via the computing device, an image of the user's skin area to be diagnosed or treated; instantiating an image classification system to identify a dermatological disease from the image; and presenting one or more medical recommendations to the user based on the identified dermatological disease.

17 Claims, 16 Drawing Sheets

Related U.S. Application Data

(60) Provisional application No. 62/654,111, filed on Apr. 6, 2018.

(51) Int. Cl.
*G16H 10/20* (2018.01)
*G16H 50/30* (2018.01)
*G16H 70/60* (2018.01)
*G16H 80/00* (2018.01)

(58) Field of Classification Search
CPC .... G06F 19/3418; G16H 10/00; G16H 10/40; G16H 10/60; G16H 15/00; G16H 20/00; G16H 20/40; G16H 30/00; G16H 30/40; G16H 50/00; G16H 50/20
USPC .......................................................... 705/2, 3
See application file for complete search history.

(56) References Cited

U.S. PATENT DOCUMENTS

| | | | |
|---|---|---|---|
| RE43,433 E * | 5/2012 | Iliff | G16H 10/60 600/300 |
| 9,864,838 B2 | 1/2018 | Goltra | |
| 10,362,985 B2 * | 7/2019 | Rundo | A61B 5/444 |
| 10,413,232 B2 * | 9/2019 | Stamnes | A61B 5/1079 |
| 2003/0105959 A1 | 6/2003 | Matyas et al. | |
| 2004/0117215 A1 * | 6/2004 | Marchosky | G16H 10/60 705/3 |
| 2010/0316263 A1 * | 12/2010 | Hamza | G06K 9/52 382/117 |
| 2011/0270044 A1 | 11/2011 | Kimmel et al. | |
| 2013/0110532 A1 * | 5/2013 | Upadhyayula | G06F 19/328 705/2 |
| 2013/0132308 A1 | 5/2013 | Boss et al. | |
| 2014/0046889 A1 * | 2/2014 | Biem | G16H 50/20 706/46 |
| 2014/0058986 A1 * | 2/2014 | Boss | G06Q 50/00 706/12 |
| 2014/0146190 A1 | 5/2014 | Mohammadi et al. | |
| 2015/0003699 A1 * | 1/2015 | Davis | G16H 50/20 382/128 |
| 2016/0290926 A1 * | 10/2016 | Notingher | G01J 3/027 |
| 2017/0011192 A1 | 1/2017 | Arshad et al. | |
| 2017/0055863 A1 | 3/2017 | Baumann et al. | |
| 2017/0109486 A1 * | 4/2017 | Tran | G06Q 20/18 |
| 2017/0246473 A1 | 8/2017 | Marinkovich et al. | |
| 2017/0323064 A1 | 11/2017 | Bates | |
| 2018/0055368 A1 | 3/2018 | Noto et al. | |
| 2018/0096686 A1 | 4/2018 | Borsutsky et al. | |
| 2018/0137249 A1 * | 5/2018 | Eggebraaten | G16H 10/60 |
| 2018/0314930 A1 * | 11/2018 | Ho | G06N 5/003 |
| 2019/0231249 A1 * | 8/2019 | Dascalu | A61B 5/0095 |
| 2019/0252074 A1 * | 8/2019 | Datla | G06F 16/90324 |

FOREIGN PATENT DOCUMENTS

| | | | |
|---|---|---|---|
| WO | WO-2017/058848 A1 | 4/2017 | |
| WO | WO-2017/167704 A1 | 10/2017 | |
| WO | WO-2018/005316 A1 | 1/2018 | |
| WO | WO2018/146688 * | 8/2018 | ............... G06T 7/00 |

OTHER PUBLICATIONS

Mensink et al., Distance-Based Image Classification: Generalizing to new classes at near-zero cost, IEEE Transactions on Pattern Analysis and Machine Intelligence, Institute of Electrical and Electronics Engineers, 2013, 35 (11), pp. 2624-2637.*

Snell et al., Prototypical networks for few-shot learning, 31st Conference on Neural Information Processing Systems (NIPS 2017), pp. 1-11 (2017).*

Kharazmi, Pegah et al., Automated Detection and Segmentation of Vascular Structures of Skin Lesions Seen in Dermoscopy, With an Application to Basal Cell Carcinoma Classification, IEEE Journal of Biomedical and Health Informatics, vol. 21, No. 6, Nov. 2017 (Year: 2017).*

Khan, Muhammad Qasim et al., Classification of Melanoma and Nevus in Digital Images for Diagnosis of Skin Cancer, Digital Object Identifier 10.1109/ACCESS.2019.2926837, Jul. 5, 2019 (Year: 2019).*

Songpan, Warrat, Improved Skin Lesion Image Classification Using Clustering with Local-GLCM Normalization, 2018 2nd European Conference on Electrical Engineering and Computer Science (EECS), DOI 10.1109/EECS.2018.00046 (Year: 2018).*

Navarro, Christian et al., Skin Disease Analysis using Digital Image processing, 2019 International Conference on Computational Intelligence and Knowledge Economy (ICCIKE) Dec. 11{12, 2019, Amity University Dubai, UAE (Year: 2019).*

Barnett et al., "DXplain: An Evolving Diagnostic Decision-Support System," JAMA, 258(1), pp. 67-74 (Jul. 3, 1987).

Bordes et al., "Learning End-to-End Goal Oriented Dialog," International Conference on Learning Representations, pp. 1-15 (2017).

Howard and Ruder, "Universal Language Model Fine-tuning for Text Classification," Proceedings of the 56th Annual Meeting of the Association for Computational Linguistics, 12 pages (May 23, 2018).

Merity et al., "Regularizing and Optimizing LSTM Language Models," International Conference on Learning Representations, 10 pages (Aug. 7, 2017).

Miller et al., "*Internist-1*, an Experimental Computer-Based Diagnostic Consultant for General Internal Medicine," The New England Journal of Medicine, 307(8), pp. 468-476 (Aug. 19, 1982).

Miller, "Computer-Assisted Diagnostic Decision Support: History, Challenges, and Possible Paths Forward," Advances in Health Sciences Education, 14(Supplement 1), pp. 89-106 (2009).

Miotto et al., "Deep Patient: An Unsupervised Representation to Predict the Future of Patients from the Electronic Health Records," Scientific Reports, 6, pp. 1-10 (May 17, 2016).

Rajkomar et al., "Scalable and Accurate Deep Learning for Electronic Health Records," Nature Partner Journals, pp. 1-10 (May 8, 2018).

Semigran et al., "Comparison of Physician and Computer Diagnostic Accuracy," JAMA Internal Medicine, 176, 2 pages (Oct. 10, 2016).

Shwe et al., "Probabilistic Diagnosis Using a Reformulation of the Internist-1/QMR Knowledge Base," Methods of Information in Medicine, 30(4), pp. 241-255 (1991).

USPTO PCT International Search Report and Written Opinion issued in International Patent Application No. PCT/US19/23381, dated Jun. 12, 2019, 25 pages.

* cited by examiner

More Information

Are there any other things you'd like to tell us about?

tire|

Fatigue (Tiredness)

Bleeding (Bleeding Retired)

Abnormal Vaginal Bleeding (Hypermenorrhoea Retired)

Eye Strain (Tired Eyes)

Bleeding After Intercourse (Postcoital Bleeding Retired)

Vaginal Sores (Vaginal Ulcertion Retired)

Dribbling Of Urine (Bladder Retention Of Urine Retired)

FIG. 11

SYSTEMS AND METHODS FOR RESPONDING TO HEALTHCARE INQUIRIES

CROSS-REFERENCE TO RELATED APPLICATIONS

This patent application is a continuation-in-part of U.S. patent application Ser. No. 16/265,799, filed Feb. 1, 2019, which claims priority to U.S. Provisional Patent Application No. 62/654,111, filed Apr. 6, 2018, each of which is hereby incorporated by reference herein in its entirety.

FIELD OF THE DISCLOSURE

The present disclosure relates generally to medical decision support systems and, more particularly, to systems and methods for responding to healthcare inquiries.

BACKGROUND OF THE DISCLOSURE

Medical decision support systems have been studied and developed over the years. See e.g., Miller, Randolph A., "Computer-Assisted Diagnostic Decision Support: History, Challenges, and Possible Paths Forward," *Advances in Health Sciences Education*, vol. 14, no. 51 (September 2009): 89-106. While there have been different approaches to designing medical decision support systems, the most successful ones fall in a category known as expert rule-based systems. Expert rule-based systems involve domain experts (e.g., case physicians) encoding medical knowledge into rules that are then executed to come up with a decision or a recommendation for a given case. The decision is provided as a ranked list of diagnosis, also called "differential diagnosis." Most expert rule-based systems encode knowledge as a bipartite graph with nodes representing findings and diagnoses, and the edges representing likelihoods of a finding given a diagnosis and/or a diagnosis given a finding.

Two well-known expert rule-based systems are Internist-1 (see e.g., Miller, R. A., H. E. Pople, and J. D. Myers, "Internist-1, an Experimental Computer-Based Diagnostic Consultant for General Internal Medicine," *The New England Journal of Medicine*, vol. 307, no. 8 (Aug. 19, 1982): 468-76) and DXplain® (see e.g., Barnett, G. Octo, James J. Cimino, Jon A. Hupp, and Edward P. Hoffer, "DXplain: An Evolving Diagnostic Decision-Support System," *JAMA*, vol. 258, no. 1 (Jul. 3, 1987): 67-74). Internist-1 and DXplain® are related to QMR (see e.g., Miller, R. A., H. E. Pople, and J. D. Myers, "Internist-1, an Experimental Computer-Based Diagnostic Consultant for General Internal Medicine," *The New England Journal of Medicine*, vol. 307, no. 8 (Aug. 19, 1982): 468-76) since Internist-1 is a precursor and DXplain® is a recent evolution. In both of Internist-1 and DXplain®, the relation between a finding and a disease is encoded into two numbers: "Evoking Strength" encodes the likelihood of a disease given a finding while "Frequency" describes how likely a symptom is to occur given a disease manifestation.

Expert rule-based systems such as the ones described above have been used to support doctors in their medical practice. However, simplified versions have also been instantiated as patient-facing applications that are sometimes called "symptom checkers." These patient systems have unreliable accuracy (see e.g., Semigran, Hannah L., David M. Levine, Shantanu Nundy, and Ateev Mehrotra, "Comparison of Physician and Computer Diagnostic Accuracy," *JAMA Internal Medicine*, vol. 176, no. 12 (Dec. 1, 2016): 1860-61) and have limited features.

Furthermore, creating a new disease in an expert rule-based system is very costly, both in terms of time and robustness. It may take weeks of several expert diagnosticians working full-time, and the resulting system can be brittle and inflexible since it cannot react to newly available data or evidence (e.g., a new disease).

Because of some of these shortcomings, there have been through the years many attempts to develop machine-learned diagnosis models. These include early approaches using Bayesian Networks (see e.g., Shwe, Michael A., Blackford Middleton, D. E. Heckerman, Max Henrion, E. J. Horvitz, H. P. Lehmann, and G. F. Cooper, "Probabilistic Diagnosis Using a Reformulation of the INTERNIST-1/QMR Knowledge Base," *Methods of Information in Medicine*, vol. 30, no. 4 (1991): 241-255) to the most recent ones using Deep Learning models (see e.g., Rajkomar, Alvin, Eyal Oren, Kai Chen, Andrew M. Dai, Nissan Hajaj, Peter J. Liu, Xiaobing Liu, et al., "Scalable and Accurate Deep Learning for Electronic Health Records," ArXiv: 1801.07860 [Cs], Jan. 24, 2018; Miotto, Riccardo, Li, Brian A. Kidd, and Joel T. Dudley, "Deep Patient: An Unsupervised Representation to Predict the Future of Patients from the Electronic Health Records," *Scientific Reports*, vol. 6 (May 17, 2016)). These machine-learned approaches have been mostly academic research exercises that have not been included in commercially-available systems. Also, one of the reasons for the lack of practical applicability of the machine-learned models is that a medical decision support system not only needs to have a model that predicts a diagnosis given a set of inputs, but also needs to provide an efficient way to navigate the path towards an optimal diagnosis by asking the right questions. That is easier to implement in rule-based systems, but gets more complicated for more complex diagnosis models.

More generally, these existing technologies have many shortcomings that make them less useful in a patient-facing application. Some relate to the user interface and experience or the lack of key features, while others relate more to the performance or accuracy of the system itself.

In view of the foregoing, it may be understood that there may be significant problems and shortcomings associated with current medical decision support systems. Accordingly, there is a need for addressing these shortcomings and introducing a whole suite of innovations that make it possible to implement a patient-facing medical decision support system.

SUMMARY OF THE DISCLOSURE

Techniques for responding to a healthcare inquiry from a user are disclosed. In one particular embodiment, the techniques may be realized as a method for responding to a healthcare inquiry from a user, according to a set of instructions stored on a memory of a computing device and executed by a processor of the computing device, the method comprising the steps of: classifying an intent of the user based on the healthcare inquiry; identifying the intent as a need to obtain a dermatological diagnosis or treatment; soliciting, from the user and via the computing device, an image of the user's skin area to be diagnosed or treated; instantiating an image classification system to identify a dermatological disease from the image; and presenting one or more medical recommendations to the user based on the identified dermatological disease.

In accordance with other aspects of this particular embodiment, the image classification system may use a Deep Learning technique to identify the dermatological disease.

In accordance with further aspects of this particular embodiment, the image classification system may use prototypical clustering networks to identify the dermatological disease.

In accordance with additional aspects of this particular embodiment, the method may further comprise, prior to the presenting step, determining a confidence level of each of the one or more medical recommendations.

In accordance with other aspects of this particular embodiment, the method may further comprise, when the confidence level is below a predetermined threshold, eliciting, by a conversational engine, information from the user.

In accordance with further aspects of this particular embodiment, the eliciting step may include invoking a natural language understanding engine.

In accordance with additional aspects of this particular embodiment, the information may be in the form of at least one of text, speech, imagery, sound, and medical test results.

In accordance with other aspects of this particular embodiment, the information may include at least one of user's medical history and the user's symptoms.

In accordance with further aspects of this particular embodiment, the conversational engine may be one of a diagnosis conversational engine, an information conversational engine, a referral conversational engine, and a treatment conversational engine.

In accordance with additional aspects of this particular embodiment, the presenting step may comprise invoking at least one of a diagnosis engine and a knowledge base.

In accordance with other aspects of this particular embodiment, the method may further comprise, prior to the presenting step, seeking approval or revision of the one or more medical recommendations by a medical expert.

In another particular embodiment, the techniques may be realized as a system for responding to a healthcare inquiry from a user, the system comprising: memory for storing instructions; and a processor configured to execute the instructions to: classify an intent of the user based on the healthcare inquiry; identify the intent as a need to obtain a dermatological diagnosis or treatment; solicit, from the user and via the computing device, an image of the user's skin area to be diagnosed or treated; instantiate an image classification system to identify a dermatological disease from the image; and present one or more medical recommendations to the user based on identified dermatological disease.

The present disclosure will now be described in more detail with reference to particular embodiments thereof as shown in the accompanying drawings. While the present disclosure is described below with reference to particular embodiments, it should be understood that the present disclosure is not limited thereto. Those of ordinary skill in the art having access to the teachings herein will recognize additional implementations, modifications, and embodiments, as well as other fields of use, which are within the scope of the present disclosure as described herein, and with respect to which the present disclosure may be of significant utility.

BRIEF DESCRIPTION OF THE DRAWINGS

In order to facilitate a fuller understanding of the present disclosure, reference is now made to the accompanying drawings, in which like elements are referenced with like numerals. These drawings should not be construed as limiting the present disclosure, but are intended to be illustrative only.

FIG. 11 shows an example of an autocomplete operation in accordance with an embodiment of the present disclosure.

DETAILED DESCRIPTION OF EMBODIMENTS

Figure 1:
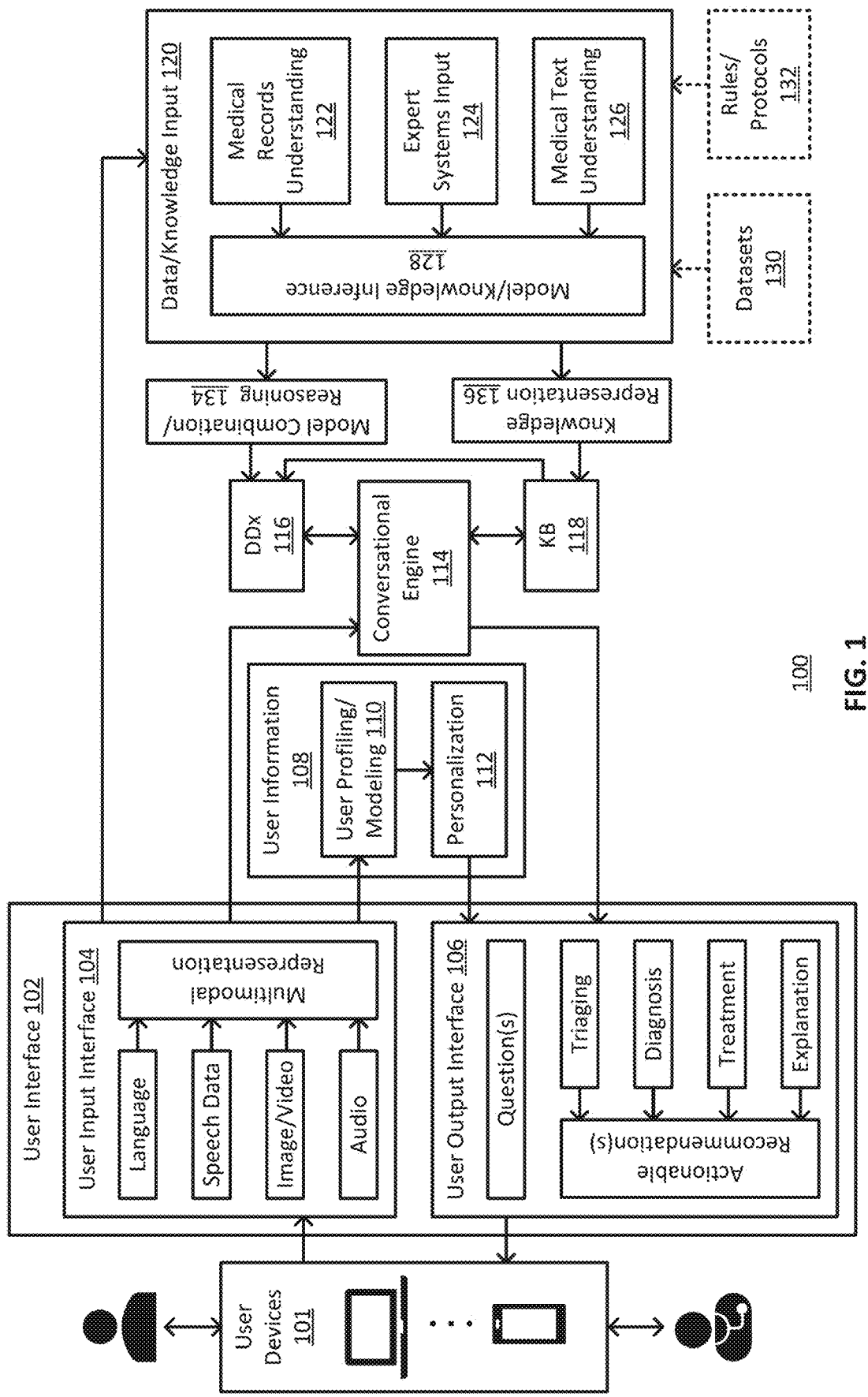
FIG. 1 illustrates a medical decision support system in accordance with an embodiment of the present disclosure.

FIG. 1 illustrates a medical decision support system 100 in accordance with an embodiment of the present disclosure. The system 100 may interface with a user (e.g., a patient, a medical expert, etc.) via the user interface 102. The user may access the user interface 102 through at least one of a plurality of user devices 101, which may comprise a laptop, a smartphone, a tablet, smart speakers (e.g., Amazon Echo, Google Home, etc.), digital assistants, etc. The user interface 102 may be in communication with the system 100 backend, which may comprise a user information module 108, a conversational engine 114, a differential diagnosis engine (DDx) 116, a knowledge base (KB) 118, and a data/knowledge input module 120.

The user interface 102 may be divided into a user input interface 104 and a user output interface 106. The user input interface 104 may allow input from the user in different modalities, including, but not limited to, natural language (of the user), speech data (e.g., from a smart speaker), image/video, and audio. The user input interface 104 may integrate the different modalities into a multimodal representation to be processed by the conversational engine 114, as described below. The user output interface 106 may provide the user (i.e., a patient or a medical expert), on at least one of a plurality of user devices 101, with one or more actionable recommendations, such as triaging, diagnosis, treatment, or explanations, as described below. Sometimes, the user output interface 106 may also need to present the user with questions in order to elicit additional and the right kind of information such that the system 100 is able provide a confident recommendation.

The user information module 108 may include two submodules—a user profile/modeling submodule 110 and a personalization submodule 112. The user profile/modeling submodule 110 may create and/or update a user's profile with all relevant information available about the user from the user input interface 104. The user profile/modeling submodule 110 may be built on the notion of creating a personalized health record. The personalization submodule 112 may use the user's profile from the user profile/modeling submodule 110 in order to optimize the relevance of the recommendations and information that the system 100 is to present to the user.

The conversational engine 114 may be in charge of understanding user's input(s), reasoning about the user's input(s), and deciding what is the most appropriate output(s) after consulting with the DDx 116 and the KB 118. The DDx 116 may produce a ranked list of possible diagnoses given any number of findings, which may be symptoms expressed by the patient as well as their history, demographics, etc. In an embodiment, the DDx 116 may be based on rules in a knowledge based codifying probabilistic relationships between symptoms/findings and diseases. In another embodiment, the DDx 116 may be based on machine-learned models deriving relations between symptoms/findings and diseases from historical medical records. In yet another embodiment, the DDx 116 may be based on machine-learned models deriving both probabilities and relationships from historic medical records. In another embodiment, the DDx 116 may be based on machine-learned models learned from mixed data that includes at least one of synthetic data generated by a pre-existing expert system, electronic medical records, manual cases, labeled cases from the diagnosis engine, as will be described below. Alternatively, the DDx 116 may comprise all these embodiments working in ensemble such that each embodiment may operate based on a current state of knowledge independently, and offer possible responses along with a confidence and a value estimate. Additionally, there may be an ensemble arbitrator to choose a response out of the possible responses or a collection of responses from the different embodiments, that is best for the user or circumstance given a match or a mismatch between the possible responses, and the value and the confidence estimate each embodiment expresses in its corresponding response. The ensemble arbitrator may learn a weight to use for each possible response from each of embodiment of the DDx 116 based upon history.

The KB 118 may be a graph representation of medical concepts and relations between the medical concepts, allowing for concepts, modifiers, relations, and hierarchies. The initial set of concepts in the graph may be derived from the Systematized Nomenclature of Medicine Clinical Terms (SNOMED CT) ontology standard, and represented by unified medical language system (UMLS) concept unique identifiers (CUIs). Relations in the graph may be machine-learned from different sources. The KB 118 may represent normalized medical concepts, which include at least one of: entities representing findings, symptoms, and conditions; modifiers representing anatomical location, severity, and temporal modifiers; weighted relations between the entities; and relations between the entities and the modifiers. The normalized medical concepts may further include a representation of models and engines as an instance of a graph with the entities and the relations; a mapping of a medical text to a knowledge base representation by using an entity recognition module; and additional knowledge sources. As will be described below, the entity recognition component module is configured to translate health-related text into medical entities and modifiers. The KB 118 may grow and may incorporate future concepts as needed. The following is an example of some concepts and relationships that may be represented in the KB 118:

```
findings:
    {
        "id": 31,
        "name": "hip pain",
        "expression": "22253000|pain:363698007|Finding
        site=304907005|hip",
    }
diseases:
    {
        "id: 7,
        "name": "acute renal failure",
        "expression": "14669001|acute renal failure",
    }
relationships:
    "304907005|hip": [
        {
            "is_a": 39352004|joint
        }
    ]
edges:
    {
        "disease": 7,
        "finding": 31,
        "metadata": {
            "strength": 0.8284268201196736
        }
    {
```

The above exemplary graph illustrates a relationship between a finding 31 ("hip pain") under the "findings" node and a disease 7 ("acute renal failure") under the "diseases" node. The relationship is captured under the "edges" node of the graph with a relative "strength" of 0.83 (i.e., it is closely related or "common"). Moreover, each node may capture additional information under the "expression" field. For example, the finding 31 ("hip pain") is of type "pain" and is located in the "hip." Also, under the "relationships" node, "hip" is defined as a "joint". The KB 118 may also provide an application programming interface (API) with a set of operations that allow to navigate the graph. A sequence of exemplary operations may be:

get_children: joint→[knee, elbow, shoulder, ankle]
refine
"knee pain"→"severe knee pain"
"joint pain"→["knee pain", "elbow pain", "ankle pain"]

expansion: "knee swelling"→["knee pain", "knee inflammation", "knee . . . ", "hand swelling", "joint swelling", " . . . swelling"]

In this example, the "refine" operation allows to retrieve entities of a parent node type from the KB 118. For example, when the "refine" operation is applied to "joint," the KB 118 returns different kinds of joints; when applied to "joint pain," the KB 118 returns different kinds of joint pains; and when applied to "knee pains," the KB 118 returns variations of knee pain. The "expansion" operation does a traversal of the graph and returns any valid modification for any of the concepts in the expression. For example, when the "expansion" operation is applied to "knee swelling," the KB 118 returns all possible types of knee conditions, as well as swellings.

Both the DDx 116 and the KB 118 may be informed by the data/knowledge input module 120. The DDx 116 may further be informed by the KB 118. The data/knowledge input module 120 may intake different data sources and models, such as datasets 130 and rules/protocols 132. Examples of the datasets 130 are electronic medical records (EMRs) (also known as electronic health records (EHRs)) and Wikidoc (www.wikidoc.org). The rules/protocols 132 may come from medical experts, from decision support systems such as DXplain®, for example. In addition to the datasets 130 and the rules/protocols 132, the data/knowledge input module 120 may also intake information and data from the user input interface 104.

The data/knowledge input module 120 may include a medical records understanding submodule 122, an expert systems input submodule 124, a medical text understanding submodule 126, and a model/knowledge inference submodule 128. The medical records understanding submodule 122 may parse and understand medical data in EMRs by applying natural language processing (NLP) technologies to doctors' notes and encoding all other available information as features that may be used in later modeling stages. The expert systems input submodule 124 may ingest arbitrary knowledge graphs and encode them in a way that may be understood and combined with other existing models. The medical text understanding submodule 126 may apply NLP technologies to extract concepts and relations from existing medical text resources to construct knowledge base graphs and diagnosis models.

The model/knowledge inference submodule 128 may be a service model that includes functionalities that is needed by the other submodules. One such example of the functionalities may be to allow the medical records understanding submodule 122, the expert systems input submodule 124, and/or the medical text understanding submodule 126 to interface with the model combination/reasoning module 134, which informs the DDx 116. The model combination/reasoning module 134 may select the optimal model needed for making a particular diagnosis. In an embodiment, model combination/reasoning module 134 may respond to rules about which of the existing models respond better to a kind of diagnosis. For example, a model that has been trained on medical records from a pediatric hospital will be preferred when building a diagnosis for a child. In another embodiment, the model combination/reasoning module 134 may be an ensemble trained on data such that responses from different models are combined with different weighs corresponding to the models' abilities to respond to previous similar cases. Another functionality of the model/knowledge inference submodule 128 may be to interface with the knowledge representation module 136, which informs the KB 118. The knowledge representation module 136 may use the output of the data/knowledge input module 120 and organize the output in a representation that is usable by the other modules. For instance, the knowledge representation module 136 may provide processed knowledge and structures from the data/knowledge input module 120 to the KB 118.

Figure 2:
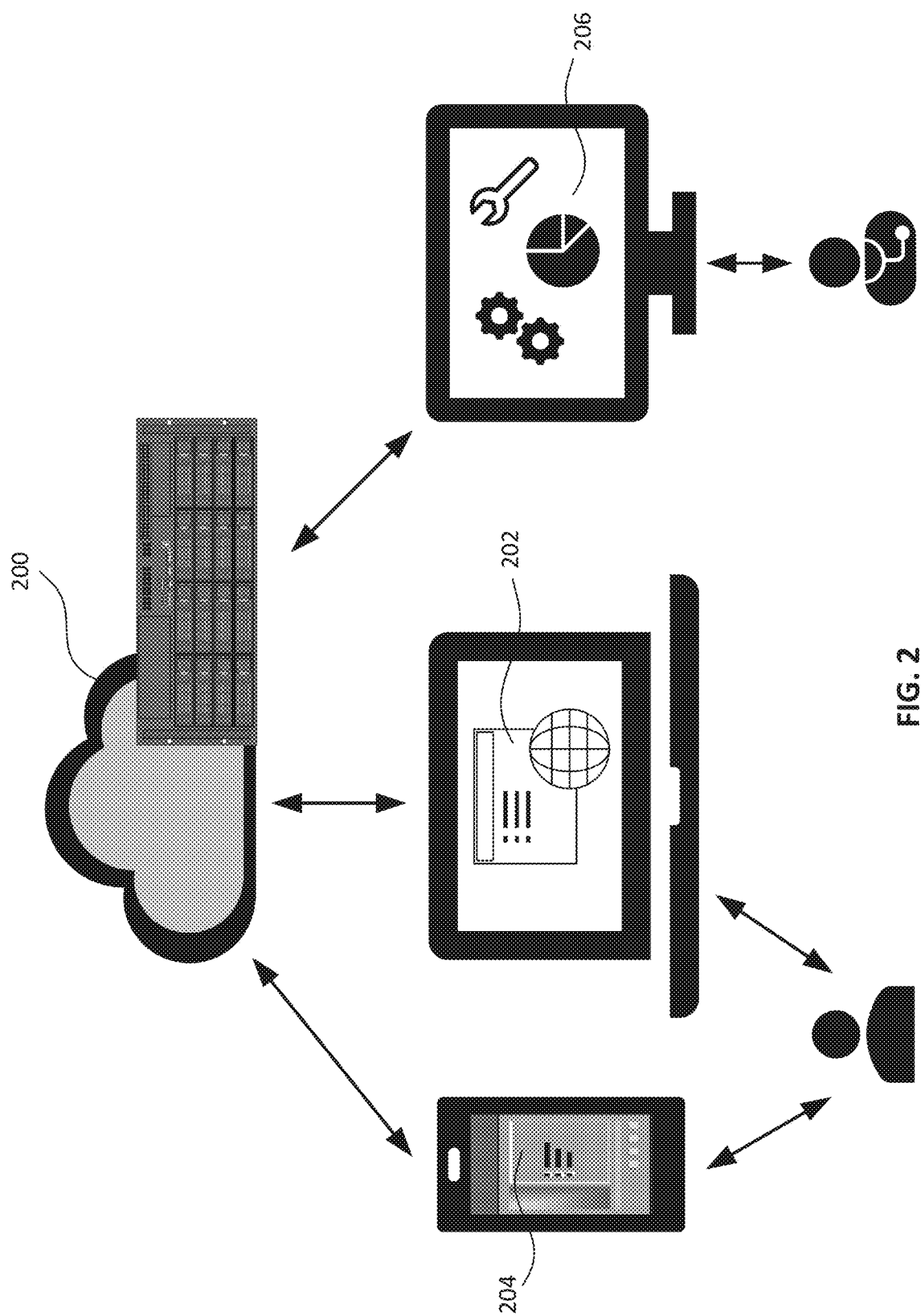
FIG. 2 illustrates interactions between a medical decision support system and patients and medical experts in accordance with an embodiment of the present disclosure.

FIG. 2 illustrates interactions between a medical decision support system 200 and patients and medical experts in accordance with an embodiment of the present disclosure. The system 200 may be a cloud service system. The system 200 may encompass the system 100 and enable a plurality of client applications. For example, a patient-facing application may be deployed as a web-based application 202, as well as a mobile device application 204. The system 200 may include a plurality of tools 206, for example via a computer, providing functionalities for medical experts to access data generated by patients during their sessions with the system 200.

Figure 3:
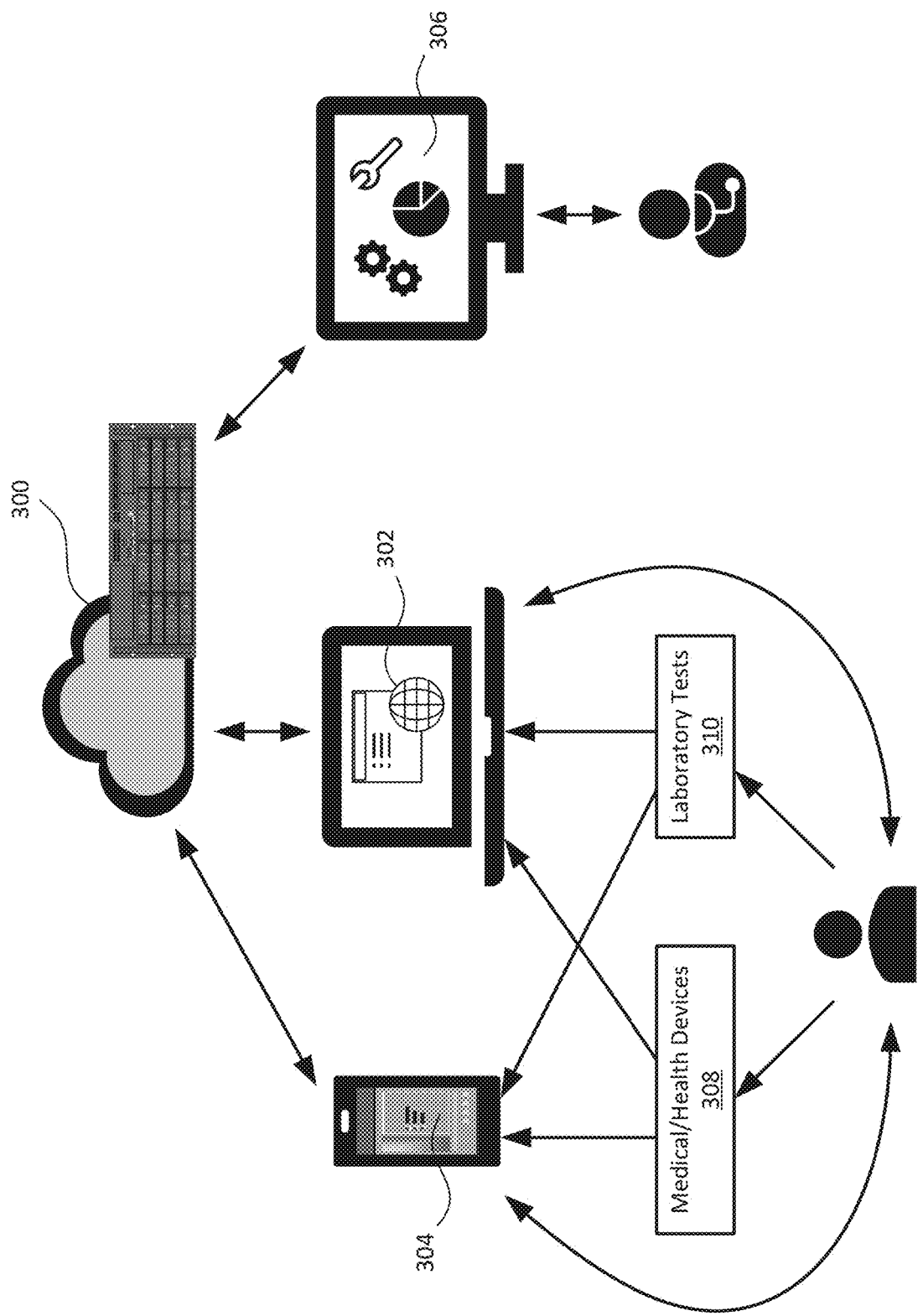
FIG. 3 illustrates interactions between a medical decision support system and patients and medical experts in accordance with an embodiment of the present disclosure.

FIG. 3 illustrates interactions between a medical decision support system 300 and patients and medical experts in accordance with an embodiment of the present disclosure. The system 300 may be a cloud service system. The system 300 may encompass the system 100 and enable a plurality of client applications. While a patient may interact directly with a web-based application 302 and/or a mobile device application 304, the cloud service system 300 may also provide the ability to input data from medical and health devices 308 (e.g., a heart-rate monitor, an at-home blood pressure device, etc.), as well as results from laboratory tests 310 (e.g., from conventional laboratories, at-home or in-pharmacy instruments, etc.). The system 300 may include a plurality of tools 306, for example via a computer, providing functionalities for medical experts to access data generated by patients during their sessions with the system 300 and/or to access patient data from the medical and health devices 308 and the laboratory tests 310.

Figure 4:
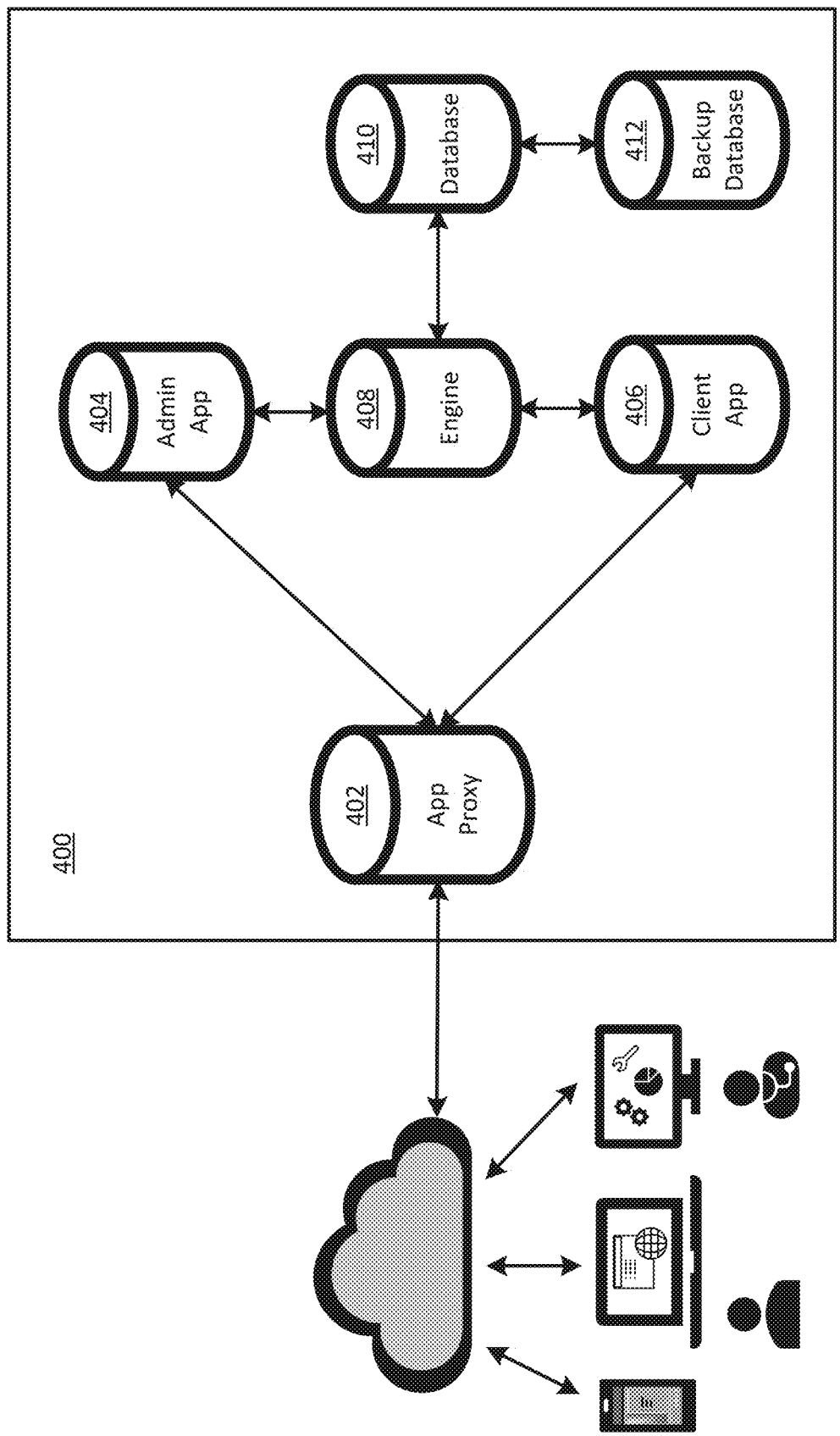
FIG. 4 illustrates an infrastructure of a medical decision support system in accordance with an embodiment of the present disclosure.

FIG. 4 illustrates an infrastructure 400 of a medical decision support system in accordance with an embodiment of the present disclosure. The infrastructure 400 may be exposed to users via an application proxy (App Proxy) node 402, which may route requests to an administrative application (Admin App) 404 and/or a client application (Client App) 406, while restricting access to other internal resources. The App Proxy node 402 may be a Hypertext Transfer Protocol (HTTP) server, which may handle both serving web resources and acting as a proxy between the public internet and the Admin App 404 and the Client App 406. An example of such an HTTP server is an nginx server. An engine 408 may reside in a cloud service system. For example, the engine 408 may be deployed as a Python Flask server running on a cloud service system (e.g., Google Cloud), while the Admin App 404 and the Client App 406 may share a frontend stack, which may for example be built on React, a JavaScript library. The infrastructure 400 may be built on top of a Docker container platform. Each of the major components in the infrastructure 400 may be packaged and deployed as a self-contained container, avoiding the need to keep development and production environments in synchronization in terms of tools, dependencies, etc.

The engine 408 may be the backend server for a medical decision support system (e.g., the system 100, 200, or 300), and may provide the following functionalities:

Functionalities available on the Admin App 404 and the Client App 406
  Packaging all supported knowledge bases (e.g., Sontag, VDDX, Wiki) in the medical decision support system Implementing algorithms that operate on the knowledge bases to provide functionalities such as next question to be posed to a patient and diagnosis to be presented to the patient Logging user activity and managing user session history Providing messaging support between patients and medical experts As shown in FIG. 4, the engine 408 may be in communication with a database 410, which in turn may be in communication with a backup database 412. The database 410 may store all data transactions including user and doctor information. The backup database 412 may be a secondary storage where a daily snapshot of the database 410 may be stored, for example, for security purposes.

Figure 5:
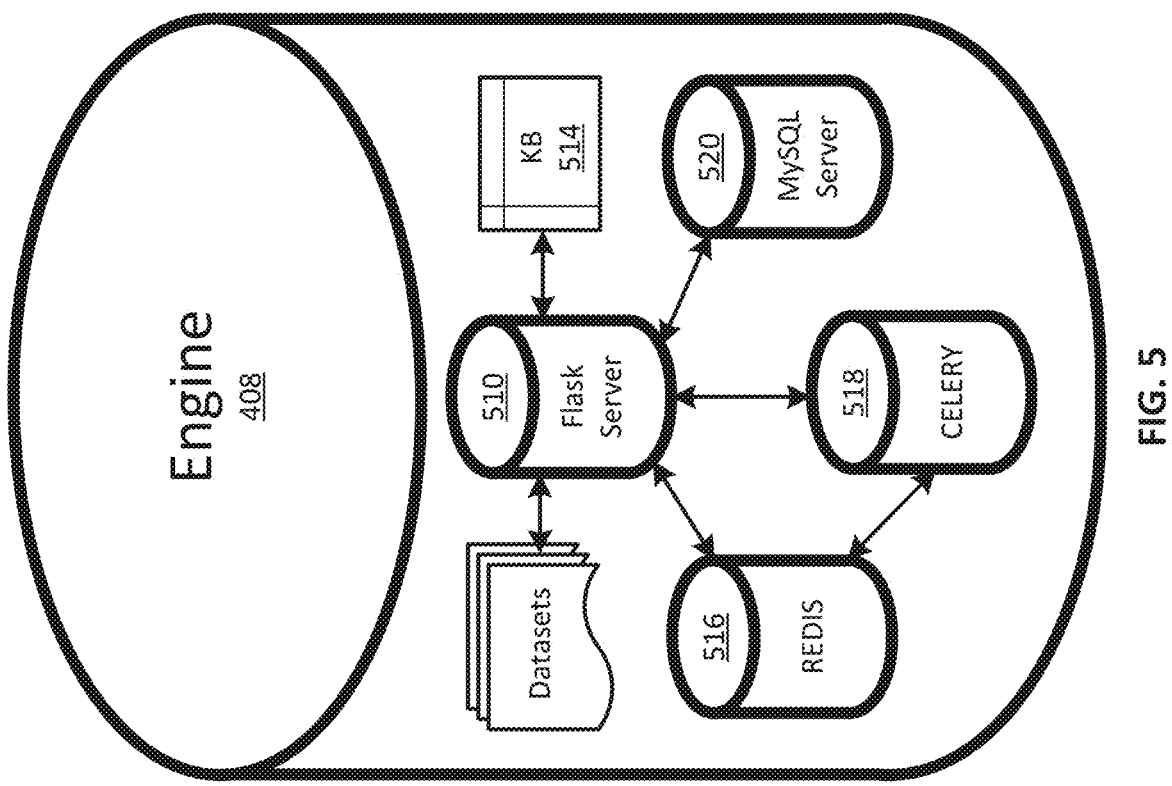
FIG. 5 illustrates an exemplary architecture a backend server for a medical decision support system in accordance with an embodiment of the present disclosure.

FIG. 5 illustrates an exemplary architecture of the engine 408 in accordance with an embodiment of the present disclosure. The engine 408 may be a Python server built on a Flask server 510. Flask aims to be a lightweight, but extensible framework for building Python services and servers. Flask libraries, such as authentication, logging, persistence, HTTP request/response, etc., are available for functions and functionalities needed to build the engine 408. The engine 408 may be deployed, locally and/or on a cloud service system, as a self-contained Docker image, which may be a composition of several smaller Docker images with specific functionalities. The engine 408 may include an in-memory knowledge base (KB) 514 that may contain relevant datasets imported into internal data structures. At runtime, the Flask server 510 may perform only read operations on the KB 514. The KB 514 is served as a binary SQLLite file that gets loaded into memory on startup. The engine 408 may further include a MySQL server 520, which may host databases used by the Flask server 510. In an embodiment, only user data (e.g., patient profiles and their interaction sessions) may be stored in the MySQL server 520, while the KB 514 is served as a binary file. A Celery 518, which may be included in the engine 408, is an asynchronous task queue/job queue based on distributed message passing. The Celery 518 may be focused on real-time operation, and may also supports scheduling. The Celery 518 may be used in the engine 4408 to schedule and execute non-blocking tasks, such as sending messages, thereby allowing the Flask server 510 to respond to users' requests quickly without being blocked by slow calls that may be executed asynchronous. A Redis 516, which also may be include in engine 408, is an in-memory data structure store that may be used as a database, cache, and message broker. The engine 408 may schedule asynchronous tasks by writing objects into the Redis 516, to which the Celery 518 may be continuously listening for changes and handling/executing any tasks as they arrive.

Figure 6:
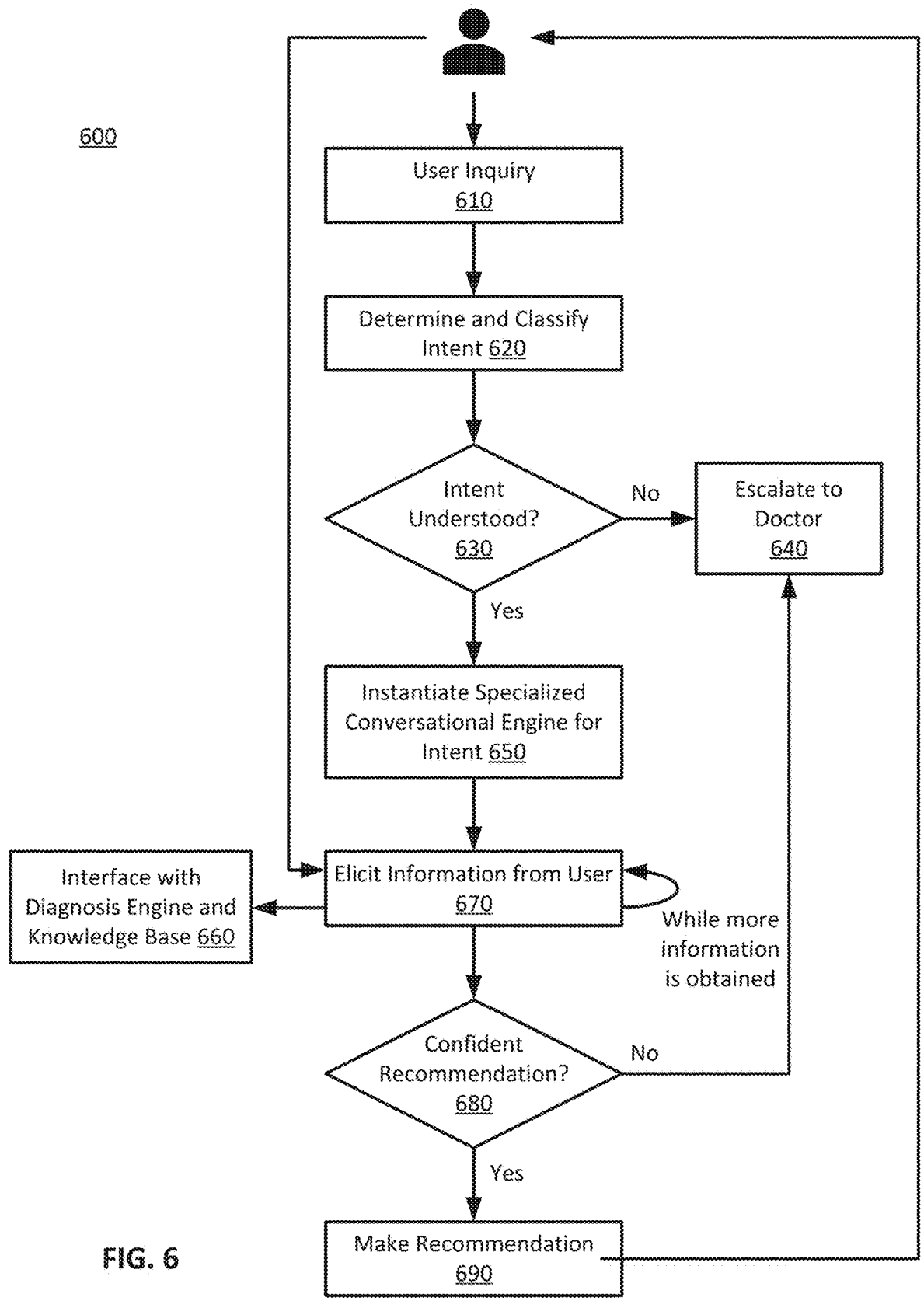
FIG. 6 is a flowchart illustrating a method for responding to a healthcare inquiry from a user using a medical decision support system in accordance with an embodiment of the present disclosure.

FIG. 6 is a flowchart illustrating a method 600 for responding to a healthcare inquiry from a user (e.g., a patient) using a medical decision support system (e.g., the system 100, 200, or 300) in accordance with an embodiment of the present disclosure. The method 600 begins at step 610 with the user making a healthcare inquiry. At step 620, the method 600 determines and classifies the intent of user's inquiry as one of a plurality of intent classifications (as described below), using a conversational engine (e.g., conversational engine 114). The method 600 proceeds to step 630, where a decision is made as to whether the user's intent is understood. If the user's intent is not understood (in which case, no trustworthy actionable recommendation may be provided with some degree of confidence), the user's inquiry is escalated to a doctor, at step 640. However, if the user's intent is understood at step 630, the method 600 moves to step 650 and instantiates one of a plurality of specialized conversational engines for the intent, based on the intent classification. Then, at step 660, based on interfacing with a diagnosis engine (e.g., the DDx 116) and a knowledge base (e.g., the KB 118), the method 600 elicits more information from the user (if needed). Once all needed information is obtained from the user, the method 600 decides, at step 680, whether a confident recommendation may be made. If a confident recommendation may not be made at step 680, the user's inquiry is escalated to a doctor, at step 640. Otherwise, a recommendation (e.g., diagnosis, referral, treatment, etc.) is made to the user at step 690. The goal of the method 600, therefore, is to provide at least one of a plurality of actionable recommendations to the user.

A medical decision support system (e.g., the system 100, 200, or 300) typically includes a software system to manage a patient dialog system to perform one or more of the following steps:

clarify question that the patient asked gather additional information, including presence or absence of additional symptoms, patient history, demographic data, etc.

establish the patient intent gather such additional details as calendar appointment details, insurance details, emergency contact information, etc.

The medical decision support systems described herein may be included in a broad category of dialog systems, with a specific focus on medical tasks. Dialog systems may be generally categorized as task-oriented (e.g., buying a plane ticket) or chatbots. Most approaches to dialog systems have used a "slot-filling" mechanism, where an initial frame with slots is defined and the goal of the dialog is to fill in those slots. See e.g., Jurafsky and Martin, "Speech and Language Processing," $2^{nd}$ edition. Research into end-to-end dialog systems using Deep Learning techniques has recently emerged. See e.g., Bordes et al., "Learning End-to-End Goal-Oriented Dialog," *International Conference on Learning Representations,* 2016. The systems described herein may use a combination of both approaches with a goal of offering not only an accurate, but also a natural medical conversation.

Figure 7:
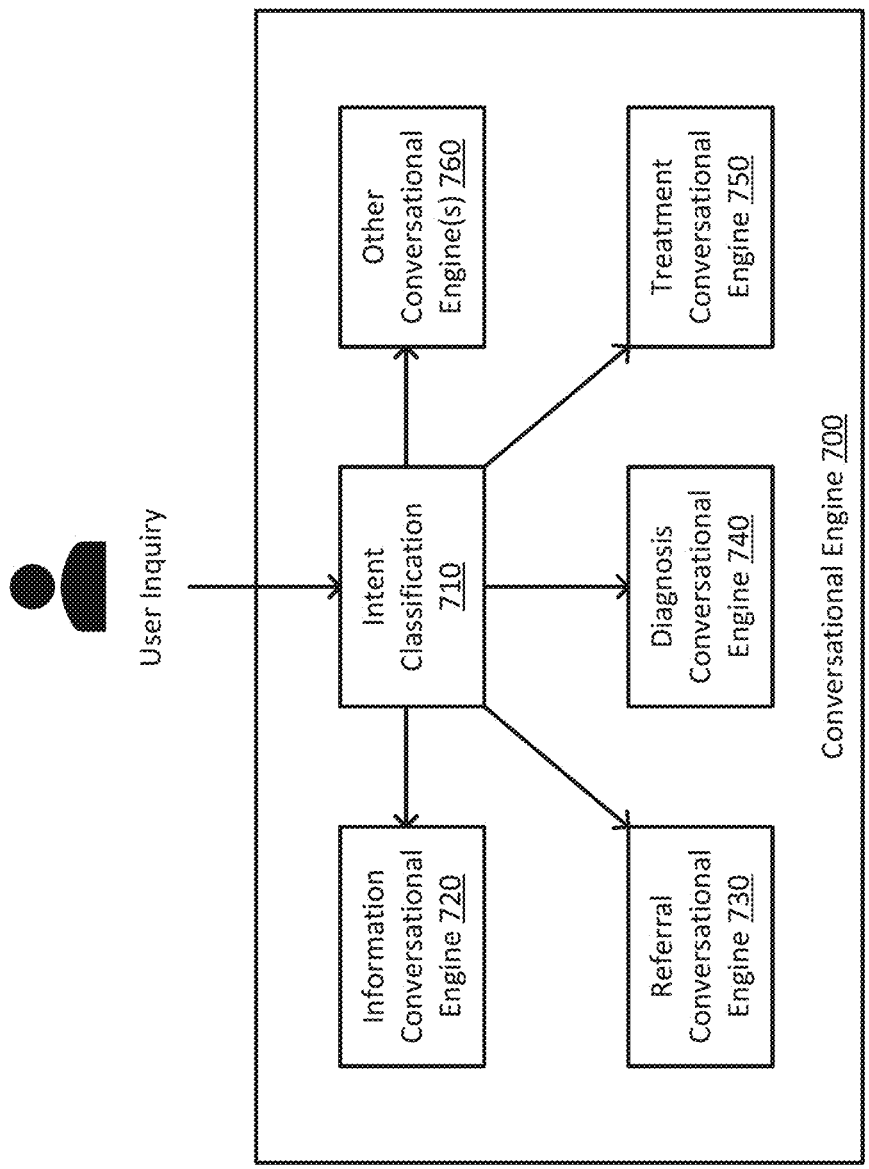
FIG. 7 illustrates the operation of an intent classification module within a conversational engine in accordance with an embodiment of the present disclosure.

A patient dialog system may be comprised of a series of templates for the information required, and formulations for questions to pose to the patient to elicit that information. A model may represent the system's current estimate of the patient objectives, and chooses next questions to be asked with a combination of the following objectives:

clarifying, quantifying, or modifying a previous response prompting for additional inputs that the patient may consider important or relevant identifying symptoms that may discriminate between different possible diagnoses or patient states, and asking whether the patient is experiencing any such symptoms, from general to specific (e.g., pain, joint pain, elbow pain, shooting elbow pain, etc.)

asking questions about symptoms that may serve to strengthen or weaken the hypotheses about specific diseases that may be present asking for personal health history, including but not limited to gender, age, ethnicity, previous diseases, vaccinations, current and past prescriptions, ancestry, and ancestors' health status, etc.

prompting for input of, or connection to existing health or test records to integrate into the model In order to offer the above functionalities, the system may implement a dialog engine (e.g., the conversational engine 114) that may include an intent classification module. FIG. 7 illustrates the operation of an intent classification module 710 within a conversational engine 700, in accordance with an embodiment of the present disclosure. The conversational engine 700 may be an example of the conversational engine 114. The intent classification module 710 may classify a user's intent into a finite set of "intents." Those intents include, but are not limited to, diagnosis, doctor referral, prescription or treatment recommendation, and information on a given disease. The intent classification module 710 may be built by using a combination of encoded rules and machine-learned classifier models. Encoded rules help the intent classification module 710 to identify patterns that are then treated as a single entity. For example, "right lower back" may be identified as an anatomical part plus two location modifiers. Entities and processed raw text (through, e.g., embeddings) may then be fed into a supervised classification component that has been trained using thousands of labeled examples. As shown in FIG. 7, the intent classification module 710 may then route the user query to one of a plurality specialized conversational engines—information conversational engine 720, referral conversational engine 730, diagnosis conversational engine 740, treatment conversational engine 750, other conversational engine(s) 760—, each configured to handle a classified intent.

Figure 8:
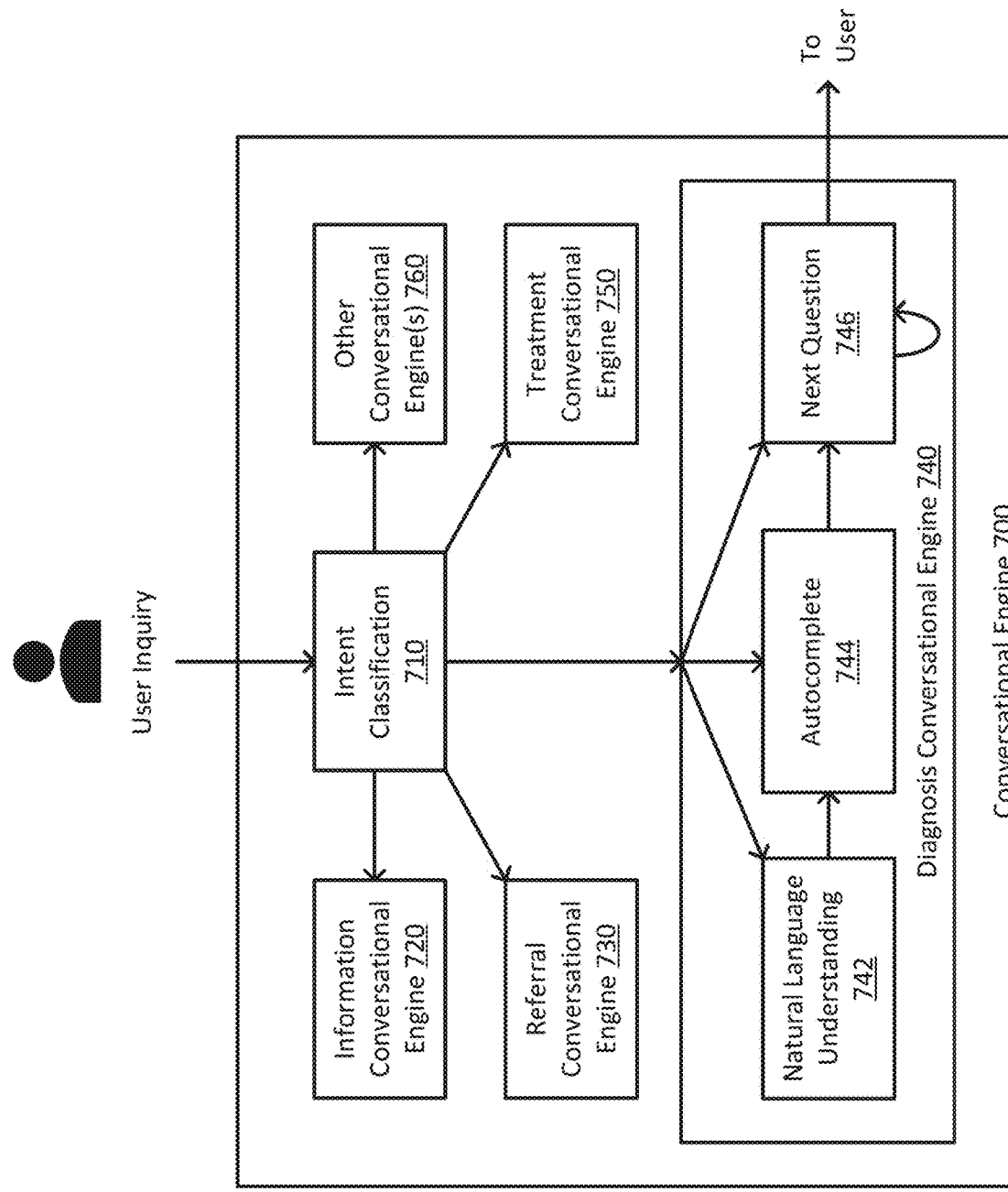
FIG. 8 illustrates a structure of a specialized conversational engine in accordance with an embodiment of the present disclosure.

Each specialized conversational engine may be built using a combination of a natural language understanding (NLU) module, an autocomplete module, and a next question module. For instance, FIG. 8 illustrates the structure of the diagnosis conversational engine 740 in accordance with an embodiment of the present disclosure. As can be seen in FIG. 8, the diagnosis conversational engine 740 may include a natural language understanding module 742, an autocomplete module 744, and a next question module 746.

Generally, for each specialized conversational engine, an NLU module may operate with unstructured natural language inputted as text, which may include textual representations of other modalities such as voice transformed into text through a speech-to-text system. In order for the NLU module to understand and decide on next steps, it may apply an entity recognition algorithm that may recognize words and extract relevant medical concepts including modifiers, quantifiers, and negations. Entities may be mapped to a knowledge base unique identifier. Therefore, the output of the NLU module is a structured representation of the user query in the form of a combination of identifiers, which may be interpreted to determine next steps according to rules in each of the specialized conversational engines.

Figure 9:
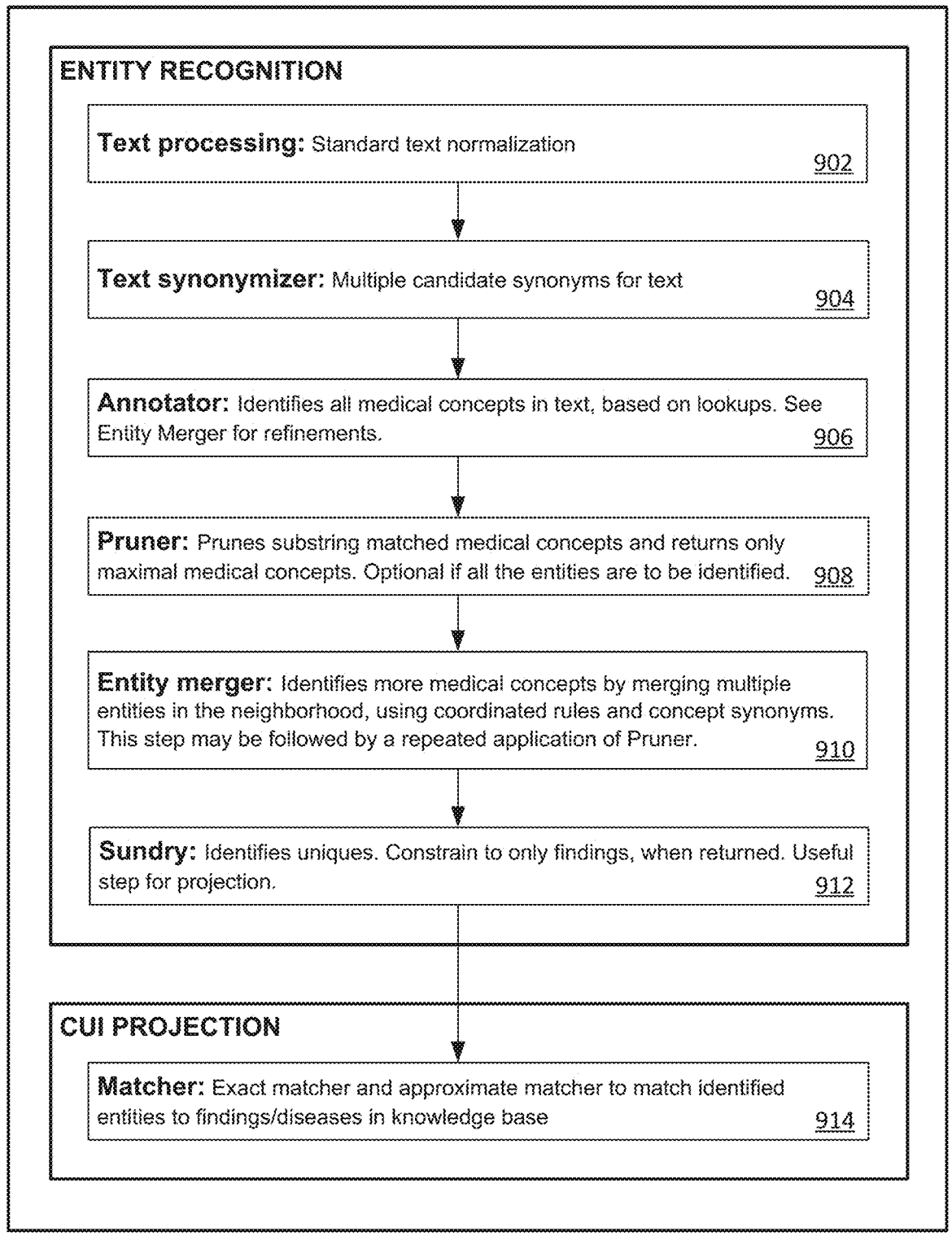
FIG. 9 is a flowchart for an exemplary entity recognition algorithm that may be employed by a natural language understanding module in a specialized conversation engine in accordance with an embodiment of the present disclosure.

FIG. 9 is a flowchart for an exemplary entity recognition algorithm 900 that may be employed by an NLU module in a specialized conversational engine in accordance with an embodiment of the present disclosure.

The entity recognition algorithm 900 starts with the text processing step 902. The text processing step 902 includes information retrieval (IR) processing, which involves removing, from text input by a user, various punctuations and standardization of certain tokens. Unlike in standard IR processing, the text processing step 902 does not remove stop words. Stop words tend to function as a bridge to connect entities. Stop words may be removed, if needed, in the pruner step 908, described below.

The entity recognition algorithm 900 then moves to the text synonymizer step 904. The text synonymizer step 904 is used to generate various synonymous ways of representing the processed text from the text processing step 902. For example, the text may be split into a collection of overlapping K-grams (K=1 to 10) using a sliding window. The location of each K-gram in the text may be preserved. Each K-gram phrase may be synonymized by lookups on Wordnet, word-by-word. When there are multiple words in the phrase that have synonyms, all possible combinations may be maintained, by constructing the combinations recursively. Some phrases may not have synonyms, while others may have many.

Following the text synonymizer step 904 is the annotator step 906, which is used to identify all entities in the free text. That is, all phrases and their synonyms are identified. A dictionary data structure may be used for fast lookups. Maintaining K-grams of various lengths and their locations in the input text may facilitate the annotator step 906.

Once the annotator step 906 completed, the entity recognition algorithm 900 moves the pruner step 908. At the pruner step 908, two operations are performed. First, entities that are sub-entities of another identified entity are pruned. For example, for the user text "knee pain," the entity corresponding to "knee" and "pain" are removed, and only the entity corresponding to "knee pain" is kept. Second, entities that can correspond to stop words such as "in" are pruned.

Next comes the entity merger step 910. The UMLS is not always consistent in concept representation. For example, UMLS may have concept "knee pain," but not "pain in the knee" as a synonymous. Through analysis on a large number of extractions, a small number of rules or patterns may be captured that are effective in capturing the main concepts that are of interest. For example, these rules may include the following code:

```
<body system> = {"Body Part, Organ, or Organ Component",
"Tissue", "Body Location or Region",
        "Body Space or Junction", "Body System", "Anatomical
        Structure"}
    <findings> = {"Finding", "Sign or Symptom", "Body Substance",
"Disease or Syndrome"}
    # <findings>|stop|<body system>
    # <body system>|stop|<findings>
    # <body system>|stop|Qualitative Concept
    # Sign or Symptom|stop|Organism Function
        # Example: pain|with|urination, pain|with|periods
    # Body System|stop|Pathologic Function
        # Example skin||bleeding|
    # Pathologic Function|stop|Body System
        # Example |bleeding|into|skin or |bleeding||skin|
```

The Pruner step may be important to increase coverage. The output of Pruner step may be used to identify entities that are in the vicinity of each other that satisfies one of these rules, and where stop is stop words. If so, the entities may be merged and annotated, using the annotator step 906. During the entity merger step 910, the chances for matches are also increased by using the UMLS synonyms of two entities, and taking their cross-product combinations. This may further improve identification. At the end of the entity merging step 910, the pruner step 908 may be run again, for further clean up. It is worth noting that, along this process, the location of the merge in original free text is maintained.

In the subsequent sundry step 912, when the text is large, redundant entities are removed, based on CUIs of the entities identified. The returned list of entities may be restricted to be only those defined as findings.

Lastly, in the matcher step 914, the output from the sundry step 912 is matched to engine specific findings, in two ways: (1) exact match on the CUIs between the entities and findings in knowledge base; and (2) when (1) is not present, approximate match based on a number of matching, missing, and mismatching entities between the candidates (with mismatching penalized more than missing).

Figure 10:
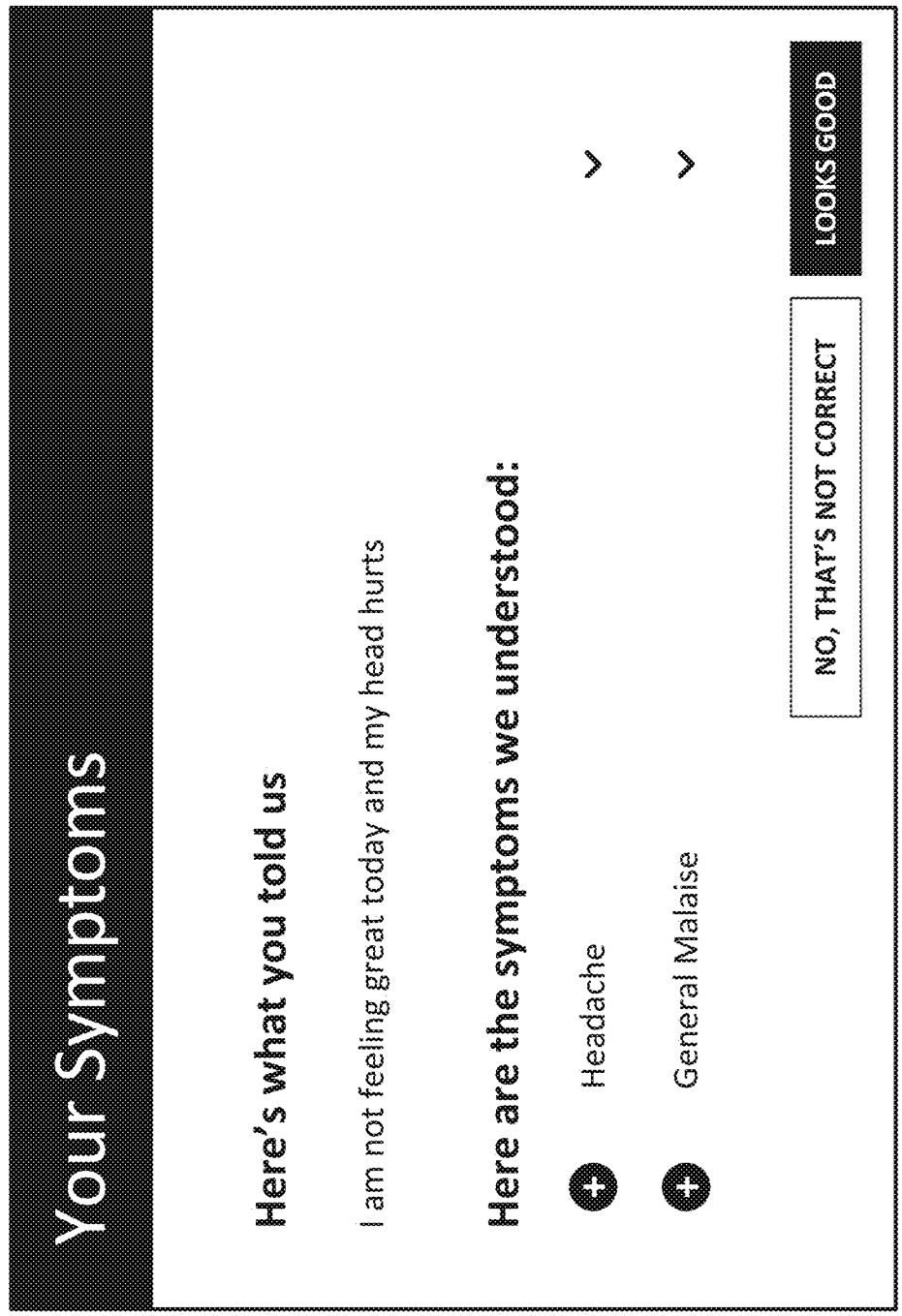
FIG. 10 shows an example of an entity extraction in accordance with an embodiment of the present disclosure.

FIG. 10 shows an example of an entity extraction in accordance with an embodiment of the present disclosure. As can be seen, if the phrase "I am not feeling great today and my head hurts" is input by a user, an entity recognition algorithm within an NLU module of a specialized conversational engine may return "headache" and "general malaise" as possible symptoms to the user.

An autocomplete module may allow a specialized conversational engine to suggest medical concepts or entities coming from the knowledge base (e.g., KB 118) as a letters from a user are being inputted in the system. The suggestions not only include words that include the letters entered by the user, but also words that include the letters among their synonyms. FIG. 11 shows an example of an autocomplete operation in accordance with an embodiment of the present disclosure.

The next question module in a specialized conversational engine may be able to determine the optimal next question to ask a user given the current state of the dialog between the user and the specialized conversational engine. The way that the optimal next question may be determined depends on the specifics of each specialized conversational engine, but it generally may be based on either predetermined frames or a entropy minimization algorithm. As an example of the predetermine frames, the referral conversation engine (see FIG. 7) may instantiate a frame with the necessary information (location, preferred time, preferred gender, specialty, etc.) and will determine a next question in order to fill in the blank slots in this frame. As an example of an entropy minimization next question approach, the diagnosis conversational engine (see FIGS. 7 and 8) may initially formulate a differential diagnosis and determine a next question by minimizing the entropy difference of the existing hypothesis. In other words, the goal is to minimize the entropy of the differentials. Before asking a particular question, this is given by $$H_{p(d|\mathcal{F}^t)}(d) = -\sum_{k=1}^{K} p(d = k|\mathcal{F}^t) \log p(d = k|\mathcal{F}^t)$$

where $F^t$ is the collection of the current findings and $p(d|F^t)$ is the posterior probability of disease d given the current findings. Once a given question is asked the entropy can be written as:

$$H_{p(d|\mathcal{F}_{t,f})}(d) = 0.5 * [H_{p(d|\mathcal{F}_{t,f=1})}(d) + H_{p(d|\mathcal{F}_{t,f=0})}(d)]$$

where 0.5 assumes an equal probability of a patient answering positively or negatively to a question, but could in fact be a probability distribution. Given this, the goal of the next question algorithm is to find f* by maximizing the following expression:

$$f^* = \arg\max_{f} H_{p(d|\mathcal{F}^t)}(d) - \tilde{p}(f = 1) H_{p(d|\mathcal{F}^{t,f})}(d)$$

In order to understand and reason about medicine, and have meaningful dialogs/conversations with patients, the system needs to have a representation of medical concepts. This involves having a knowledge base, and tools to convert or translate from any language representation to the internal knowledge graph representation. For example, the NLU module described above in a specialized conversational engine needs to convert natural language into a list of identifiers from the knowledge base. But, that is also true for natural language generated by doctors, or structured information coming from electronic medical records or an external knowledge base.

The language of medicine also includes tools to map text to knowledge base representation (as described in the NLU module above) and to navigate a knowledge base graph in different directions (e.g., "find related nodes" or "find parent of").

An important feature of a medical decision support system (e.g., system 100, 200, or 300) is a diagnosis engine (e.g., DDx 116). According to an embodiment, a multi-class classifier on co-occurrence of medical concepts in EMRs may be extracted. This produces a graph of medical concepts and edges between them, where the edge weights model the probability of co-occurrence of, for example, a disease given a symptom. Given such a graph, a diagnosis algorithm may be devised. The probability of a finding being present given a disease may be estimated as follows:

$$p(f_j = 1|d = k) = \begin{cases} \alpha_{j,k}, & \text{if in graph} \\ \beta, & \text{otherwise} \end{cases},$$

$$\beta = .0001 \approx .01 \times \min_{j,k} \alpha_{j,k}$$

where $\alpha_{j,k}$ are the learned weights and $\beta$ is a very small number.

Other information, but symptoms, such as patient demographics or disease prevalence, may be incorporated, as follows:

$$p(d,f,\text{age},\text{gender}) = p(f|d,\text{age},\text{gender}) p(\text{age}|d) p(\text{gender}|d) p(d)$$

In order to calculate the posterior probability of the diseases, Bayes rule may be invoked. The compute probability may be used to rank the differential diagnosis given the currently available information.

A medical decision support system (e.g., system 100, 200, or 300) may incorporate several engines working in ensemble. These engines may include rule-based engines, wherein rules in a knowledge base specify the strength of relationship between a symptom/finding, and diseases that may cause such symptoms. Those rule-based systems are derived from existing medical literature by using a combination of manual curation from expert physicians and statistical techniques.

Additionally, engines that are based on models learned from data may be included. Such models quantify the relation between symptoms and diseases observed in real-world data. The models are trained using various medical data such as anonymized EMRs from research databases or university hospitals, and from introspecting on the data collected in feedback and follow-up from the engine's own interaction with patients. Sources of bias in the samples that drive the models may be quantified, and the models may be corrected for known and estimated bias. The models may incorporate disease and symptom prevalence in the general population, and may include how those statistics vary in specific subpopulations by demographic, geography, calendar, social connections, etc. In one embodiment, the models are constrained to quantify relationships identified by the rule-based engines. In another embodiment, the models are allowed to infer knew relationships that have never been encoded as an explicit rule.

Figure 12:
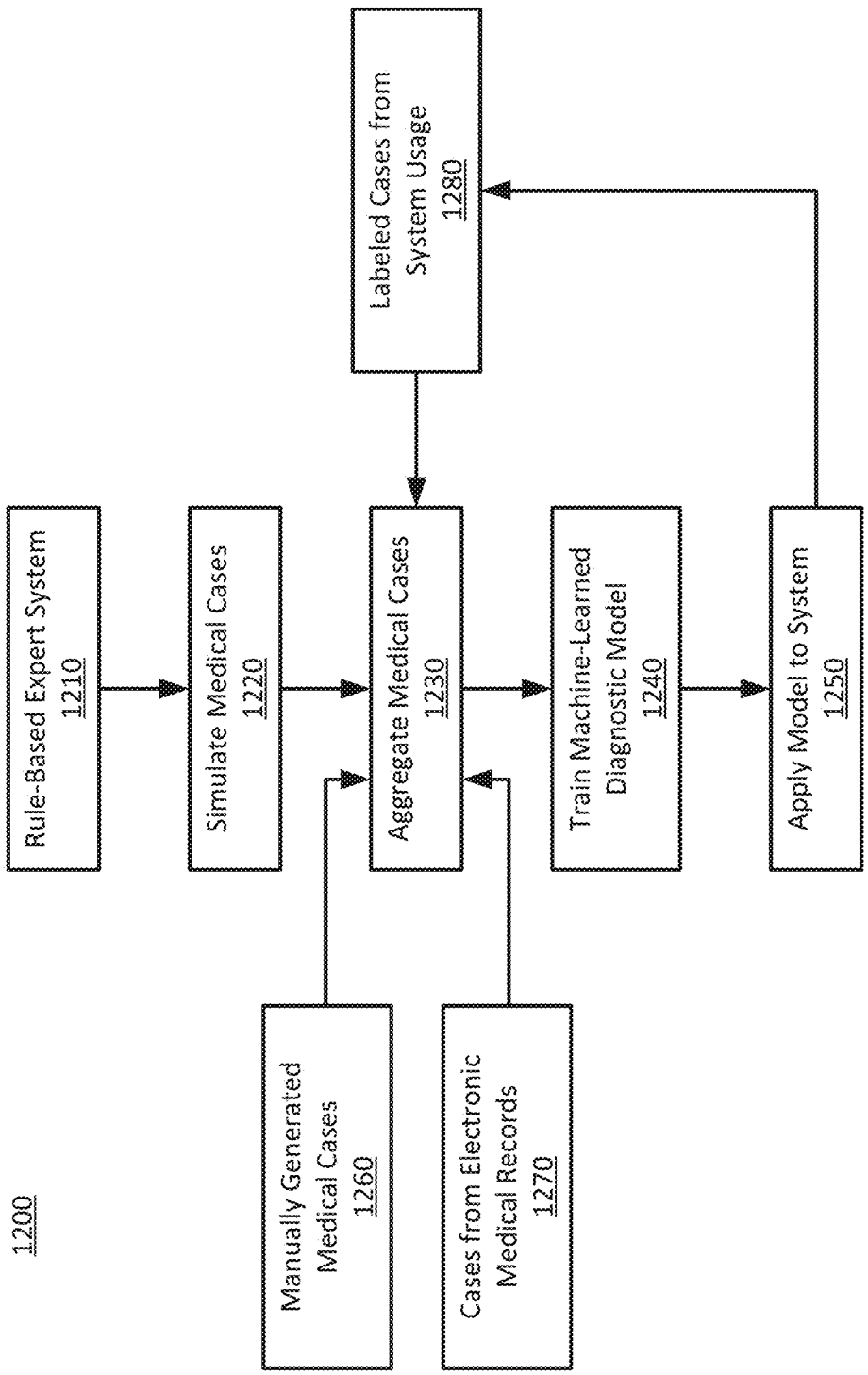
FIG. 12 is a flowchart illustrating a method of training a machine-learned model for a diagnosis engine in accordance with an embodiment of the present disclosure.

FIG. 12 illustrates a method 1200 of training a machine-learned model for a diagnosis engine in accordance with an embodiment of the present disclosure. The method 1200 may start at step 1210 with a rule-based expert system. At step 1220, the rule-based expert system is used as a generative model to create sample medical cases. At step 1240, the sample medical cases created at step 1220 are used to train a machine-learned model. The machine-learned model may then be applied to a medical decision support system at step 1250. This becomes a novel and effective way to extend and generalize expert systems that can then be combined at the data level. At step 1230, the medical cases generated by the expert system may be combined with other medical cases such as manually generated medical cases 1260, medical cases 1270 gathered from sources such as EMRs, and/or labeled medical cases 1280 from the system usage itself.

Referring back to FIG. 1, one important aspect of the system 100 is that it allows for multimodal input as part of the dialog/conversation. The system 100 allows a user/patient to input voice, images, and video as part of the dialog flow. For example, if the patient mentions having a skin rash, the system 100 may invite the patient to upload a picture. The system 100 may then perform automatic image classification and will use the output as another symptom in the diagnosis. Beyond typical multimedia documents, the system 100 may be designed to accept information coming from any medical sensor or monitoring device (e.g., heart rate monitor, blood pressure monitor, etc.).

Another important feature that the system 100 may provide is a personal health record (PHR), which is a longitudinal record of all relevant health data from history questions and from previous sessions by an individual patient, integrated with conventional medical records (EMRs, EHRs) from one or multiple healthcare providers, including both structured and unstructured doctors' notes, prescription records, etc. Unlike an EMR, a PHR may always be available to the patient to query, manage, examine, or update. The PHR is not intended to replace the specific electronic records stored at the health institutions, but rather complement and offer a holistic view of a patient's health that includes not only the aggregate of the patient's interactions with their health providers, but also more nuanced interactions with the system 100. For example, the PHR in the system 100 may include information about interactions where the patient complained or asked about a headache despite none of those might have resulted in any medical treatment. The PHR that may be offered in the system 100 remains the property of the patient and enables the patient to not only visualize, but also modify and comment in order to add more detailed or nuanced information.

As described before, the goal to the system 100 is to answer patient questions by giving a set of actionable recommendations that may include not only a diagnostic and triaging, but also referral or treatment. One important actionable recommendation that a patient that is looking for information about her health situation can get is whether she needs to visit a doctor and what is the relative urgency of the medical attention. This is accomplished by the ability of the system 100 to triage patients. In most situations, the triaging decision may be accomplished by formulating a diagnosis and classifying the diagnosis into the required attention and urgency. However, in many other situations, the simple existence of a symptom can trigger a triage recommendation. For example, chest pain on an elderly patient or high fever in an infant will trigger an automatic recommendation to visit the emergency room regardless of the confidence on the diagnosis.

Figure 13:
FIG. 13 shows a possible diagnosis output from a medical decision system resulting from symptoms entered by a user in accordance with an embodiment of the present disclosure.

Many questions from patients may be directly related to them wanting to know "what they have". The system 100 may respond in the form of a differential diagnosis. This includes a ranked list of possible conditions with an indication on how likely they are and recommended next steps. FIG. 13 shows a possible diagnosis output from the system 100 and the symptoms entered by a user that led to the output in accordance with an embodiment of the present disclosure.

While the system 100 may be designed to give up-to-date and accurate medical information, in many situations, the interaction with the patient will determine that the best path forward is for her to visit a doctor. Exemplary cases when the system 100 may decide to refer the patient to a doctor may include, but is not limited to the following:

Probability of complications are above a certain threshold
Patient requires physical examination or lab tests
The internal algorithms are not certain of what is the issue with the patient
The patient has described a critical symptom (e.g., "chest pain")

In all these cases, the system 100 may determine the best doctor to whom to refer the patient considering different variables that include everything that is known about the patient (e.g., location, healthcare provider) and their current situation (e.g., vitals, symptoms). The system 100 may present a ranked list of recommendations. The system 100 may include a database of doctors and facilities that can provide a given medical procedure or service. On the other hand, the system 100 may also provide the possibility to refer directly to in-house physicians through text or video consultation.

Given a disease, or cluster of diseases that may afflict a patient, a component of the system 100 may be designed to sort through alternative possible treatments, qualify them based upon relevance to the patient's symptoms and history, and propose possible treatments that the patient could pursue.

In follow-ups, the system 100 may collect data on treatment paths chosen by the patient, and outcomes, and use these data to learn models for which treatments to propose to other patients in the future. Some of those treatments may involve prescriptions or recommendations for over-the-counter medications. For the former, the system 100 may include referral to a healthcare professional, who can safely prescribe medications. This could be an offline prescription based on data collected, a real-time or scheduled chat or message interaction, a real-time or scheduled video consultation, or a scheduled visit for physical examination. In any of these cases, the system 100 may facilitate the paperwork of prescribing and forwarding the prescription onto a pharmacy.

The system 100 may include a database of pharmacy within which it can:
Cross-check against other medications the patient may be taking
Validate dosage for the demographics, weight, gender of the patient
Warn about possible side-effects, and incorporate follow-up on such side-effects in future interactions with the patient.
Evaluate responses to prescribed medications to confirm or reduce weight on previous conclusions about the patient's disease or condition Guide or advise on substitutions with alternatives or generic medications that may be differentially available, covered by insurance, and have differing efficacies.

Similarly, some situations may require the patient to undergo some form of laboratory testing. In some cases, the kind of testing might be available through some form of at-home procedure (e.g., blood pressure), but in many other cases the patient may need to visit a physician or pharmacist. For the former, the system 100 may refer the patient to existing third-party applications and solutions. For the latter, the system 100 may refer the patient to nearby facilities considering all the information about the patient and the current situation (e.g., how urgent the test is). In any of these cases, the system 100 may facilitate the paperwork. The system 100 may include a database of pharmacies and doctors that may provide a given test procedure.

A key to effective machine learning is generating data from which to learn. The system 100 may be designed for comprehensive follow-up with each patient, which may take the form of:

Follow-up questions to the patient asking whether their situation followed the trajectory that the system projected.

Follow-up questions to the patient asking about new, changing, or past symptoms

Follow-up questions to the patient asking whether they followed up with their doctor, and what the doctor might have confirmed or changed.

Follow-up questions to the any doctor or professional to add their corrected labels to the record.

Checking with other sources of EMR to learn results from additional testing or procedures prescribed.

Independent third-party review of interactions by expert doctors trained in classifying open-loop data and attaching a correct label to the outcome.

The system 100 has the goal of offering actionable and personalized healthcare information to patients. All use cases outlined above have some flavor of understanding a patient informational need and presenting some information about the patient's situation or the next steps to take. In order to serve those informational needs, the system 100 may include comprehensive content that may be indexed and presented in response to any question. This includes:

Information about diseases, symptoms, and treatments

Information about medications

Information about laboratory tests and other medical procedures

Information about doctors and medical facilities, including their locations and services provided by them Such content may be structured, tagged, and categorized in the system 100 so that it may be served in response to concrete informational needs and personalized in different ways.

Figure 14:
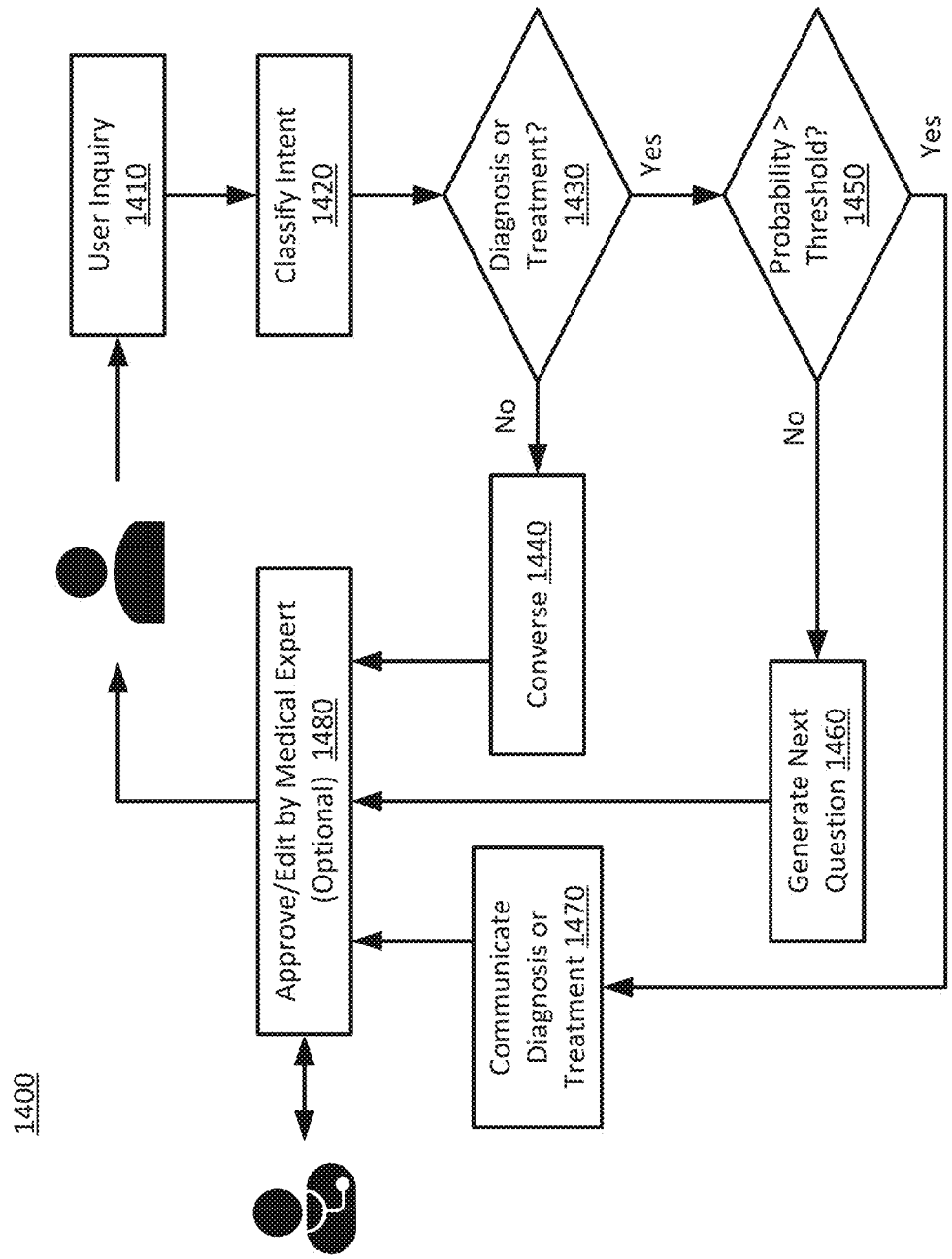
FIG. 14 is a flowchart illustrating a method for responding to a healthcare inquiry from a user using a medical decision support system in accordance with an embodiment of the present disclosure.

FIG. 14 is a flowchart illustrating a method 1400 for responding to a healthcare inquiry from a user (e.g., a patient) using a medical decision support system (e.g., the system 100, 200, or 300) in accordance with an embodiment of the present disclosure. The method 1400 begins at step 1410 with the user making a healthcare inquiry. At step 1420, the method 1400 classifies the intent of user's inquiry (e.g., using intent classification module 710). The method 1400 proceeds to step 1430, where a decision is made as to whether the user's intent is related to either a diagnosis or a treatment. If the user's intent is not related to either a diagnosis or a treatment, the method 1400 invokes a converse at step 1440. The converse generates a reasonable response based on what the medical decision support system knows about its past few interactions with the user. However, if the user's intent is related to either a diagnosis or a treatment at step 1430, the method 1400 moves to step 1450 and determines whether the confidence on a given diagnosis or treatment is above a predetermined threshold. If the confidence is below or at the predetermined threshold, the method 1400 moves to step 1460 to generate a next question, as described above, to elicit more information from the user. If the confidence is above the predetermined threshold, the method 1400 moves to step 1470 to communicate either a diagnosis or a treatment (based on interfacing with a diagnosis engine (e.g., the DDx 116) and a knowledge base (e.g., the KB 118)) to the user. Any of the response from step 1440, the next question from step 1460, and the diagnosis or treatment from step 1470 may require an optional approval/edit by a medical expert at step 1480 before being presented to the user. For example, the method 1400 may trigger step 1480 based on predefined settings (e.g., a physician may need to approve diagnosis recommendations that include diagnosis above a certain severity).

Figure 15:
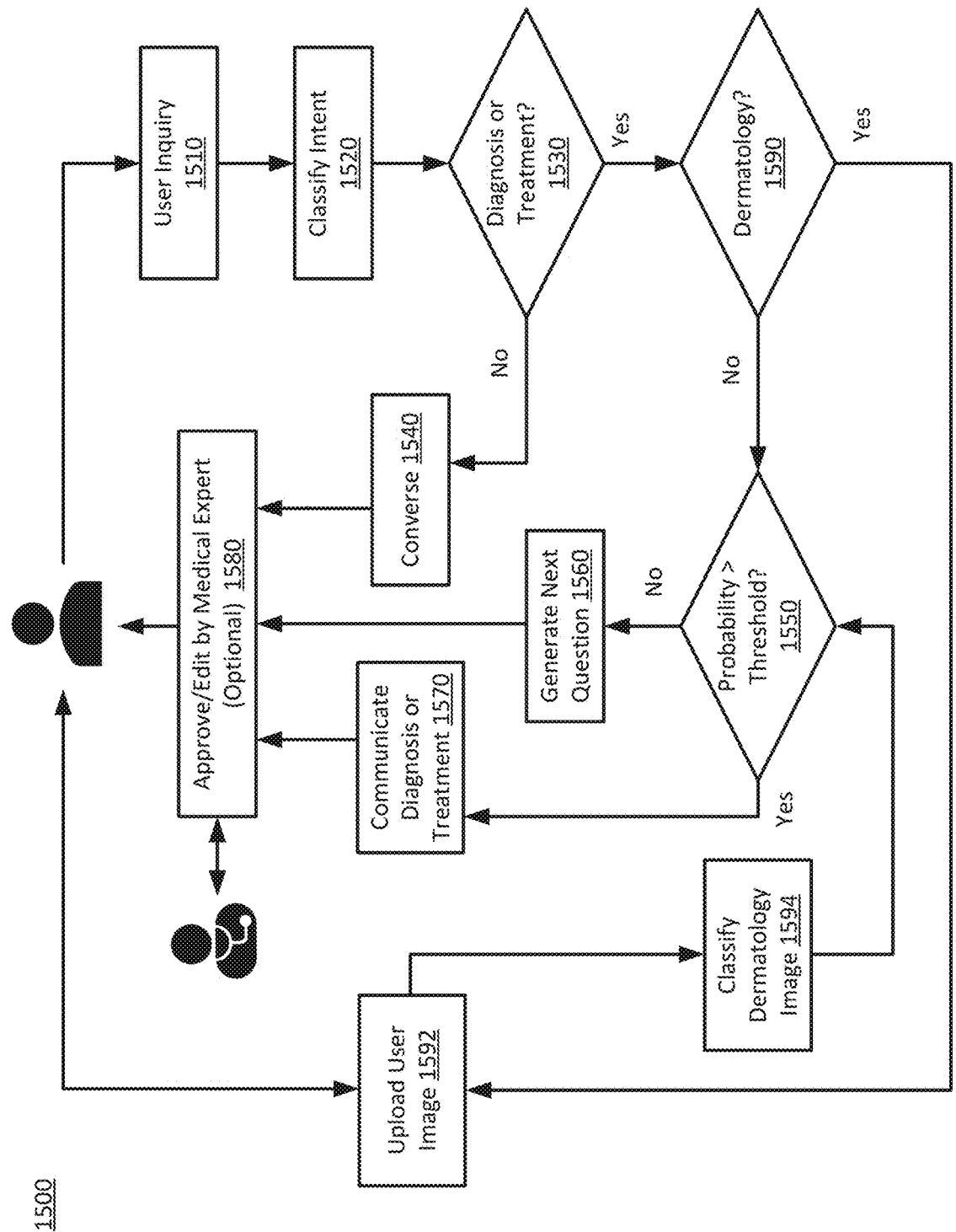
FIG. 15 is a flowchart illustrating a method for responding to a healthcare inquiry from a user using a medical decision support system in accordance with an embodiment of the present disclosure.

FIG. 15 is a flowchart illustrating a method 1500 for responding to a healthcare inquiry from a user (e.g., a patient) using a medical decision support system (e.g., the system 100, 200, or 300) in accordance with an embodiment of the present disclosure. Unlike the flowchart in FIG. 14, the flowchart in FIG. 15 specifically shows a scenario where the user's intent may be related to a dermatological diagnosis or treatment.

The method 1500 begins at step 1510 with the user making a healthcare inquiry. At step 1520, the method 1500 classifies the intent of user's inquiry (e.g., using intent classification module 710). The method 1500 proceeds to step 1530, where a decision is made as to whether the user's intent is related to either a diagnosis or a treatment. If the user's intent is not related to either a diagnosis or a treatment, the method 1500 invokes a converse at step 1540. The converse generates a reasonable response based on what the medical decision support system knows about its past few interactions with the user. However, if the user's intent is related to either a diagnosis or a treatment at step 1530, the method 1500 moves to step 1590 to determine whether the intent is dermatological in nature. If it is not, the method 1500 proceeds to step 1550 and determines whether a confidence on a given diagnosis or treatment is above a predetermined threshold. If the confidence is below or at the predetermined threshold, the method 1500 moves to step 1560 to generate a next question, as described above, to elicit more information from the user. If the confidence is above the predetermined threshold, the method 1500 moves to step 1570 to communicate either a diagnosis or a treatment (informed by a diagnosis engine (e.g., the DDx 116) and a knowledge base (e.g., the KB 118)) to the user. At step 1590, if the intent is dermatological in nature, the method 1500 solicits the user to upload an image of her dermatological disease. Once the image uploaded, the method 1500 classifies the image at step 1594, where a machine-learned image classifier produces a differential diagnosis of dermatological disease, as described below. Using the differential diagnosis, the method 1500 runs through the steps 1550-1570, as previously described. Any of the response from step 1540, the next question from step 1560, and the diagnosis or treatment from step 1570 may require an optional approval/edit by a medical expert at step 1580 before being presented to the user. For example, the method 1500 may trigger step 1580 based on predefined settings (e.g., a physician may need to approve diagnosis recommendations that include diagnosis above a certain severity).

Figure 16:
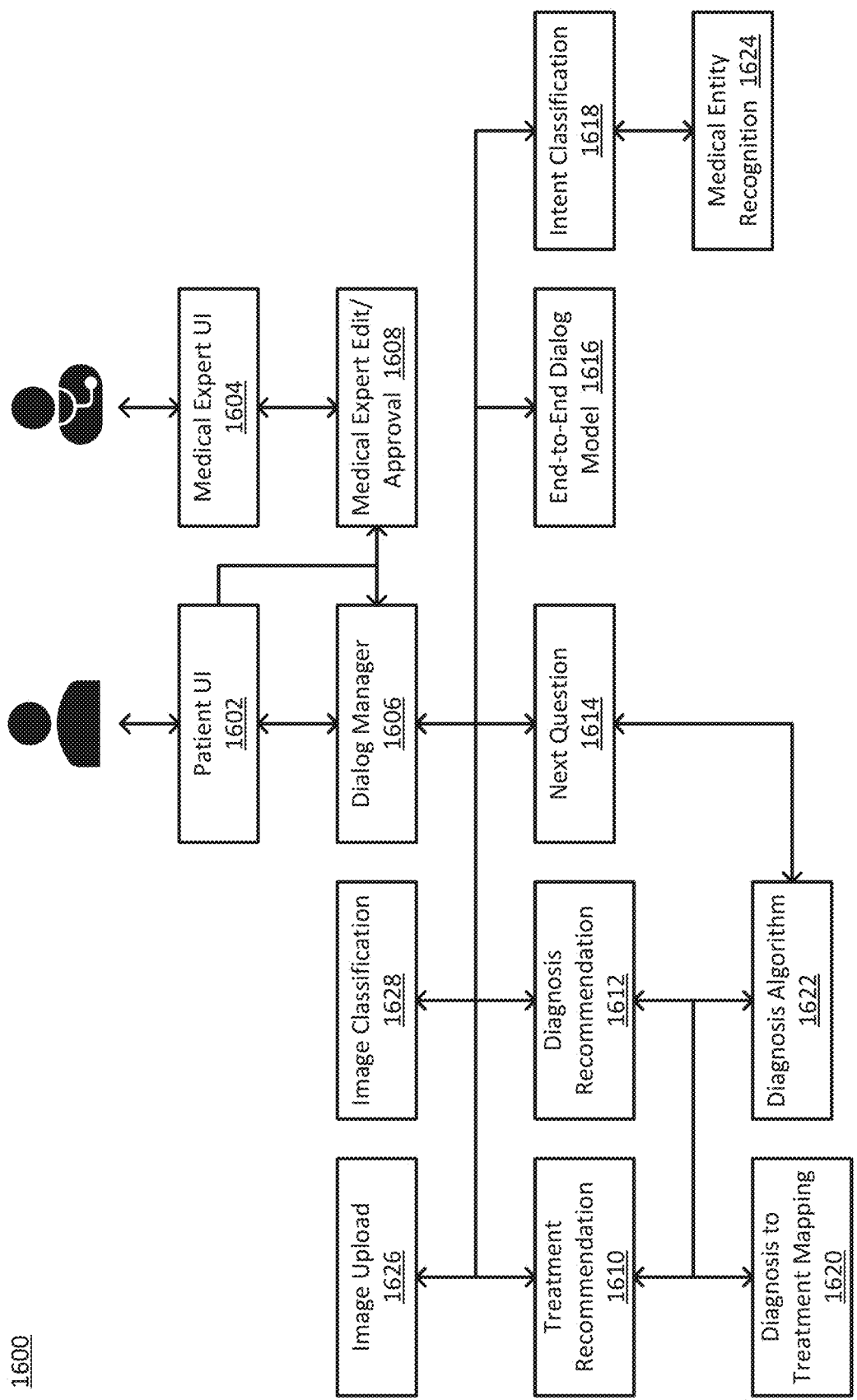
FIG. 16 illustrates an architecture of a medical decision support system in accordance with an embodiment of the present disclosure.

FIG. 16 illustrates an architecture 1600 of a medical decision support system in accordance with an embodiment of the present disclosure. The architecture 1600 may be used to perform the method 1400 or 1500, for example. As can be seen in FIG. 16, a dialog manager 1606 may be a central component in the architecture 1600. The dialog manager 1606 may communicate with the patient via a patient user interface (UI) 1602 and with a medical expert via a medical expert UI 1604.

A medical expert edit/approval module 1608 may be interposed between the dialog manager 1606 and the medical expert UI 1604. Any automatically generated information may either be sent directly to the user or pass through the medical expert edit/approval module 1608. In this module, standby physicians or professionals with equivalent training may read auto-responses or questions, and decide whether their responses or questions are of good enough quality to be directly approved or whether they may require edits.

The dialog manager 1606 may be in charge of keeping a state of a conversation between the system and the patient, and routing requests to other components. For example, the dialog manager 1606 may invoke an end-to-end dialog model 1616. The end-to-end dialog model 1616 may be a Deep Learning language model that uses a model pre-trained on a general corpuses of text (e.g., Wikipedia), and may be then fine-tuned on medical conversations between doctors and patients. This technique may be referred to as transfer learning since patterns learned on a given task or training corpus are transferred to a similar task. The model may be learned using a regularized long short-term memory network (LSTM). See e.g., Stephen Merity et al., "Regularizing and Optimizing LSTM Language Models," *International Conference on Learning Representations,* 2018. In particular, the Universal Language Model Fine-tuning for Text Classification (UMLFIT) implementation may be used. See e.g., Howard and Ruder, "Universal Language Model Fine-tuning for Text Classification," *Proceedings of the 56th Annual Meeting of the Association for Computational Linguistics,* vol. 1 (July 2018). The model may engage with patients in general conversation as well as accurately engage in conversations on topics that are common in the training set. However, it may lack an overlay of medical semantics and causal reasoning, and may have no knowledge safeguards. Such a model may be intended to respond to simple queries and determine which more detailed model in the system best suits the patient's goals and intent.

A next question module 1614 may be in charge of finding the optimal best question to ask the patient given the current state of the dialog, and, particularly, medically relevant information that is known at a given point of the dialog, as described above.

With input from the patient, the dialog manager 1606 may call an intent classification module 1618, and, depending on its response, it may decide which of the following modules described below to call up next. The intent classification module 1618 may detect whether the patient is seeking a diagnosis, or a treatment, or other help. In an embodiment, the intent classification module 1618 may be based on performing medical entity recognition, using the medical entity recognition module 1624, to recognize words related to either diagnosis or treatment (e.g., symptoms, or medications). In another embodiment, the intent classification module 1618 may be a supervised machine learning algorithm trained on interactions that have been labeled as "diagnosis", "treatment", or "other". In yet another embodiment, the intent classification module 1618 may determine that the patient's intent is related to a dermatological diagnosis or treatment, in which case the dialog manager 1606 may invoke an image upload module 1626 followed by an image classification module 1628.

The image upload module 1626 may interface with the user and prompts the user to upload an image of her dermatological disease by taking a picture with a cellphone or uploading a picture from a computer, for example.

The image classification module 1628 may be a machine-learned classifier for dermatological diseases, for example. The image classification module 1628 may be trained using a Deep Learning approach called Prototypical Clustering Networks (PCN), which is a novel approach to image classification built upon Prototypical Networks. See e.g., J. Snell, K. Swersky, and R. Zemel, "Prototypical networks for few-shot learning," *Advances in Neural Information Processing Systems,* 2017: 4077-4087). PCN formulates image classification as a low-shot learning problem. During training time, access is given to a labeled dataset corresponding to dermatological examples: $S=\{(x_1, y_1), \ldots, (x_N, y_N)\}$, where each $x_i$ is an observation, and $y_i \in \{1, \ldots, K_{base}\}$ is the label that assigns the observation to one of base classes known at training time. At test time, a small labeled dataset is provided, corresponding to $K_{novel}$ novel classes, i.e., classes distinct from $K_{base}$ classes. The objective is to learn a classifier that can predict labels for examples that may come from a combined $K_{base}+K_{novel}$ label space. PCN represents each class using a set of prototypical representations learned from the data. If $\{\mu_{z,k}\}^{Mk}$ is a collection of $M_k$ prototypes for class k, then, at test time, similarity to these representations may be measured to derive its corresponding class label. In particular, $$p(y=k|x;\phi) = \frac{\exp(-\sum_z q(z|k,x)d(f_\phi(x), \mu_{z,k}))}{\sum_{k'} \exp\left(-\sum_{z'} q(z'|k',x)d(f_\phi(x), \mu_{z',k'})\right)}$$

where $f_\phi(x)$ is the embedding function with learnable parameters $\phi$ that maps input x to a learned representation space, d is a distance function, and $q(z|k, x)$ is a soft assignment of examples to clusters from the class. When $M_k=1$ for all classes, the PCN formulation reverts to standard prototypical networks.

The goal is to learn a model with parameters $\phi$ so as to maximize the likelihood of the correct class, which may be represented as $$\phi^* = \arg\max_\phi \sum_{(x,y)} \log p(y|x; \phi)$$

and minimize its corresponding loss function $L_\phi$. Episodic training is used to learn the embedding function by optimizing the loss and updating the cluster prototypes for each class. In particular, a training epoch consists of E episodes. The following algorithm, Algorithm 1, provides details for computing the loss for one episode that is used in learning the function.

Algorithm 1 Training episode loss computation for Prototypical Clustering Networks.

1: Input: Training set $\mathcal{D} = \{(x_1, y_1), \ldots, (x_N, y_N)\}$, where each $y_i \in \{1, \ldots, K\}$. $\mathcal{D}_k$ denotes the subset of $\mathcal{D}$ containing all class prototypes, i.e., elements $(x_1, y_1) = \{\mu_{z,k}\}_{i=1}^{m_k}$ $\forall k \in \{1, \ldots, K\}$
2: Output: The loss J for a randomly generated training episode
3:
4: $V \leftarrow \text{RANDOMSAMPLE}(\{1, \ldots, K\}, N_C)$  ▷Select class indices for episode
5: for $k \in \{1, \ldots, N_O\}$ do
6:   $S_k \leftarrow \text{RANDOMSAMPLE}(\mathcal{D}_{v_k}, N_S)$  ▷Select support examples
7:   $Q_k \leftarrow \text{RANDOMSAMPLE}(\mathcal{D}_{v_k \setminus S_k}, N_Q)$  ▷Select query examples
8:   for $(x, y) \in S_k$ do  ▷Compute probabilistic assignment of x to y's cluster
9:
$$q(z \mid k, x) = \frac{\exp(-d(f_\phi(x), \mu_{z,k})/\tau)}{\sum_{z'} \exp(-d(f_\phi(x), \mu_{z',k})/\tau)}$$

10:   for $z \in \{1, \ldots, M_k\}$ do

11:
$$\mu_{z,k}^{new} \leftarrow \alpha \mu_{s,k}^{old} + (1-\alpha) \frac{\sum_{(x,y) \in S_k} q(z \mid k, x) f_\phi(x)}{\sum_{(x,y) \in S_k} q(z \mid k, x)}$$

12: $L_\phi \leftarrow 0$
13: for $k \in \{1, \ldots, N_C\}$ do
14:   for $(x, y) \in Q_k$ do 15:
$$L_\phi \leftarrow L_\phi + \frac{1}{N_C N_Q}\left[\sum_z q(z \mid k, x) d(f_\phi(x), \mu_{z,k}) + \log \sum_{k'} \exp\left(-\sum_{k'} q(z' \mid k', x) d(f_\phi(x), \mu_{z',k'})\right)\right]$$

N is the number of examples in the training set,
$K_{base}$ is the number of base classes for training,
$M_k$ is the number of clusters for class k,
$N_C \leq K_{base}$ is the number of classes per episode,
$N_S$ is the number of support examples per class,
$N_Q$ is the number of query examples per class,
RANDOMSAMPLE(S, N) denotes a set of N elements chosen uniformly at random from set S, without replacement.

In Algorithm 1, the assignment of an example within each class is given by:

$$q(z \mid k, x) = \frac{\exp(-d(f_\phi(x), \mu_{z,k})/\tau)}{\sum_{z'} \exp(-d(f_\phi(x), \mu_{z',k})/\tau)}$$

where $\tau$ is temperature parameter that controls the variance of the distribution. As the temperature is decreased, the distribution becomes peakier. As the temperature is increased, the distribution becomes flatter. The effect of temperature on the distribution has implications in the model training. The importance of $\tau$ may be understood by studying the loss function $L_\phi$ at line 15 of Algorithm 1. During training, if clusters are well-separated, $q(z \mid k, x)$ will be peaky so that each example effectively contributes to the update of a single cluster in a class, whereas if clusters overlap, $q(z \mid k, x)$ will be diffuse and the corresponding example will contribute to multiple prototypes. Therefore, during training, $\tau$ is typically set to favor peaky distributions so that clusters are learned to focus on different regions of the input space.

In episodic training, an epoch corresponds to a fixed number of episodes. In each episode, classes are sampled uniformly, which makes an inherent assumption that classes are balanced. In a setting with significant class imbalances, this translates to examples from tail classes being over-sampled, while examples from the head may be under-sampled within an epoch. This may adversely affect model training. One approach to mitigate this adverse effect is to sample classes according to class priors, which has the disadvantage of tail classes being poorly represented. Instead, an approach of refreshing the prototypes is taken. In particular, at the start of an epoch, for every class, the cluster prototypes are initialized using k-means on the learned embedding representation of examples from that class. Subsequently, in each episode, an online update scheme is used to balance between the local estimate of the prototype computed from embeddings of the current support set, and the prototypes learned so far:

$$\mu_{z,k}^{new} \leftarrow \alpha \mu_{z,k}^{old} + (1-\alpha) \frac{\sum_{(x,y) \in S_k} q(z \mid k, x) f_\phi(x)}{\sum_{(x,y) \in S_k} q(z \mid k, x)}$$

where $\alpha$ balances the episodic memory, using trade-off between memory from previous episodes and its current estimate. In particular, when $\alpha = 0$, the prototypes are memoryless while with $\alpha = 0.5$, current estimate of prototypes are as important as their previous values.

A diagnosis recommendation module 1612 may provide a differential diagnosis given what is known about the patient at a given point during the dialog. The diagnosis recommendation module 1612 may use a diagnosis algorithm 1622, an example of which is described above.

A treatment recommendation module 1610 may provide a ranked list of potential treatments given what is known about the patient at a given point during the dialog. The treatment recommendation module 1610 may use the diagnosis algorithms and then map the differential diagnosis to known treatments for a given diagnosis using a diagnosis to treatment mapping 1620.

At this point it should be noted that a medical decision support system in accordance with the present disclosure as described above may involve the processing of input data and the generation of output data to some extent. This input data processing and output data generation may be implemented in hardware or software. For example, specific electronic components may be employed in a computer server or similar or related circuitry for implementing the functions associated with a medical decision support system in accordance with the present disclosure as described above. Alternatively, one or more processors operating in accordance with instructions may implement the functions associated with a medical decision support system in accordance with the present disclosure as described above. If such is the case, it is within the scope of the present disclosure that such instructions may be stored on one or more non-transitory processor readable storage media (e.g., a magnetic disk or other storage medium), or transmitted to one or more processors via one or more signals embodied in one or more carrier waves.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of at least one particular implementation in at least one particular environment for at least one particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

The invention claimed is:

1. A method for responding to a healthcare inquiry from a user, according to a set of instructions stored on a memory of a computing device and executed by a processor of the computing device, the method comprising the steps of:
   receiving, by the computing device, the healthcare inquiry from the user;
   determining and classifying, by the computing device, an intent of the user based on the healthcare inquiry;
   identifying, by the computing device, the intent as a need to obtain a dermatological diagnosis or treatment;
   soliciting, from the user and by the computing device, an image of the user's skin area to be diagnosed or treated;
   receiving the image from the user and by the computing device;
   identifying, by the computing device, a dermatological disease from the received image by using prototypical clustering networks;
   determining, by the computing device, one or more medical recommendations based on the identified dermatological disease by invoking a knowledge base, the knowledge base being a graph representation of medical concepts and relations among the medical concepts;
   obtaining, by the computing device, a medical expert's approval of the one or more medical recommendations; and
   presenting, by the computing device, the approved one or more medical recommendations to the user.

2. The method of claim 1, further comprising, prior to the presenting step, determining, by the computing device, a confidence level of each of the approved one or more medical recommendations.

3. The method of claim 2, further comprising, when the confidence level is below a predetermined threshold, eliciting, by a conversational engine, information from the user.

4. The method of claim 3, wherein the conversational engine is a natural language understanding engine.

5. The method of claim 3, wherein the information is in the form of at least one of text, speech, imagery, sound, and medical test results.

6. The method of claim 3, wherein the information includes at least one of user's medical history and the user's symptoms.

7. The method of claim 3, wherein the conversational engine is one of a diagnosis conversational engine, an information conversational engine, a referral conversational engine, and a treatment conversational engine.

8. The method of claim 1, wherein the determining the one or more medical recommendations further invokes a differential diagnosis engine that provides a ranked list of possible diagnoses.

9. An article of manufacture for responding to a healthcare inquiry from a user, the article of manufacture comprising at least one non-transitory processor readable storage medium storing a computer program of instructions configured to be readable by at least one non-transitory processor for instructing the at least one processor to operate so as to:
   receive the healthcare inquiry from the user;
   determine and classify an intent of the user based on the healthcare inquiry;
   identify the intent as a need to obtain a dermatological diagnosis or treatment;
   solicit, from the user, an image of the user's skin area to be diagnosed or treated;
   receive the image from the user;
   identify a dermatological disease from the received image using prototypical clustering networks;
   determine one or more medical recommendations based on the identified dermatological disease by invoking a knowledge base, the knowledge base being a graph representation of medical concepts and relations among the medical concepts;
   obtain a medical expert's approval of the one or more medical recommendations; and
   present the approved one or more medical recommendations to the user.

10. A system for responding to a healthcare inquiry from a user, the system comprising:
   memory for storing instructions; and
   a processor configured to execute the instructions to:
      receive the healthcare inquiry from the user;
      determine and classify an intent of the user based on the healthcare inquiry;
      identify the intent as a need to obtain a dermatological diagnosis or treatment;
      solicit, from the user, an image of the user's skin area to be diagnosed or treated;
      receive the image from the user;
      identify a dermatological disease from the received image by using prototypical clustering networks;
      determine one or more medical recommendations based on the identified dermatological disease by invoking a knowledge base, the knowledge base being a graph representation of medical concepts and relations among the medical concepts;
      obtain a medical expert's approval of the one or more medical recommendations; and
      present the approved one or more medical recommendations to the user.

11. The system of claim 10, wherein the processor is further configured to execute the instructions to, prior to presenting the approved one or more medical recommendations, determining a confidence level of each of the approved one or more medical recommendations.

12. The system of claim 11, wherein the processor is further configured to execute the instructions to, when the confidence level is below a predetermined threshold, elicit, by a conversational engine, information from the user.

13. The system of claim 12, wherein the conversational engine is a natural language understanding engine.

14. The system of claim 12, wherein the information is in the form of at least one of text, speech, imagery, sound, and medical test results.

15. The system of claim 12, wherein the information includes at least one of user's medical history and the user's symptoms.

16. The system of claim 12, wherein the conversational engine is one of a diagnosis conversational engine, an information conversational engine, a referral conversational engine, and a treatment conversational engine.

17. The system of claim 10, wherein, to determine the one or more medical recommendations, the processor is further configured to execute the instructions to invoke a differential diagnosis engine that provides a ranked list of possible diagnoses.

* * * * *